US011351365B1

(12) United States Patent
McKeag

(10) Patent No.: US 11,351,365 B1
(45) Date of Patent: Jun. 7, 2022

(54) WIRE CLAMPING DEVICES AND METHODS FOR USE

(71) Applicant: Burt John McKeag, Kearney, NE (US)

(72) Inventor: Burt John McKeag, Kearney, NE (US)

( * ) Notice: Subject to any disclaimer, the term of this patent is extended or adjusted under 35 U.S.C. 154(b) by 346 days.

(21) Appl. No.: 16/108,811

(22) Filed: Aug. 22, 2018

Related U.S. Application Data

(60) Provisional application No. 62/551,461, filed on Aug. 29, 2017.

(51) Int. Cl.
*A61N 1/05* (2006.01)
*A61N 1/36* (2006.01)
*A61B 17/34* (2006.01)

(52) U.S. Cl.
CPC ....... *A61N 1/0558* (2013.01); *A61N 1/36071* (2013.01); *A61B 17/3401* (2013.01); *A61N 1/36017* (2013.01)

(58) Field of Classification Search
CPC .... A61N 1/0558; A61N 1/36071; A61N 1/05; A61N 1/0551; A61N 1/36017; A61B 17/3401; A61B 5/6838; A61B 5/6884; A61B 17/7076; A61B 17/0401; A61B 17/0487; A61B 17/3468; A61B 2017/0409; A61B 2017/0427; A61B 2017/0446; A61B 2017/0496; A61F 2/0811
See application file for complete search history.

(56) References Cited

U.S. PATENT DOCUMENTS

| | | | | |
|---|---|---|---|---|
| 6,387,076 B1 * | 5/2002 | Landuyt | ............... | A61M 25/02 |
| | | | | 128/DIG. 6 |
| 6,572,588 B1 * | 6/2003 | Bierman | ............... | A61M 25/02 |
| | | | | 128/DIG. 26 |
| 7,787,960 B2 * | 8/2010 | Lubenow | ............... | A61N 1/056 |
| | | | | 607/116 |
| 8,140,172 B1 * | 3/2012 | Jones | ............... | A61M 5/14276 |
| | | | | 600/375 |
| 8,998,929 B2 * | 4/2015 | Havel | ............... | A61B 17/3468 |
| | | | | 606/129 |

(Continued)

OTHER PUBLICATIONS

Definition of restraint. Merriam-Webster Dictionary, retrieved on Sep. 12, 2020; Retrieved from the Internet: < https://www.merriam-webster.com/dictionary/restraint> (Year: 2020).*

*Primary Examiner* — Gary Jackson
*Assistant Examiner* — Sebastian X Lukjan
(74) *Attorney, Agent, or Firm* — McDonnell Boehnen Hulbert & Berghoff LLP

(57) ABSTRACT

Within examples, a wire clamping device includes a base. The base includes an indentation, a first attachment component at a first end of the base, and a second attachment component at a second end of the base that is opposite the first end. The wire clamping device further includes an arm that includes a protrusion and a third attachment component that is attached to the first attachment component. The arm is configured to rotate with respect to the first attachment component to a position at which the arm is restrained by the second attachment component against the base and at least a portion of the protrusion is within the indentation or aligned with the indentation. Additional examples include a method for using the wire clamping device, a tool for opening the wire clamping device, and a method for using the tool to open the wire clamping device.

21 Claims, 38 Drawing Sheets

(56) References Cited

U.S. PATENT DOCUMENTS

| | | | | |
|---|---|---|---|---|
| 2003/0229313 | A1* | 12/2003 | Bierman | A61M 25/02 |
| | | | | 604/174 |
| 2006/0161058 | A1* | 7/2006 | Ives | A61B 5/296 |
| | | | | 600/373 |
| 2006/0271136 | A1* | 11/2006 | Wojciechowicz | ............ |
| | | | | H01R 13/5829 |
| | | | | 607/116 |
| 2010/0004642 | A1* | 1/2010 | Lumpkin | A61F 9/008 |
| | | | | 606/4 |
| 2010/0030309 | A1* | 2/2010 | Sueda | A61B 5/0488 |
| | | | | 607/117 |
| 2012/0035692 | A1* | 2/2012 | Cantion | A61N 1/0558 |
| | | | | 607/116 |
| 2013/0218205 | A1* | 8/2013 | Stanley | A61B 17/0487 |
| | | | | 606/232 |
| 2014/0121674 | A1* | 5/2014 | Staunton | A61B 17/3468 |
| | | | | 606/129 |

* cited by examiner

WIRE CLAMPING DEVICES AND METHODS FOR USE

CROSS-REFERENCE TO RELATED APPLICATION

This application claims the benefit of U.S. Provisional Patent Application No. 62/551,461, filed on Aug. 29, 2017, the contents of which are incorporated herein by reference in their entirety.

BACKGROUND

Unless otherwise indicated herein, the materials described in this section are not prior art to the claims in this application and are not admitted to be prior art by inclusion in this section.

Percutaneous spinal cord stimulation is a method for treating various pain disorders such as back pain. It is often used when more traditional methods of pain treatment and/or surgery have been ineffective, or as an alternative to narcotic pain medication. Percutaneous spinal cord stimulation generally involves producing a small puncture wound in a subject's back (e.g., via a needle), inserting a wire into the subject's epidural space through the puncture wound, and causing electric current to flow into the subject's epidural space through the wire. The electric current may stimulate various nervous tissues within the spinal cord and cause some of the subject's pain receptors to deactivate or reduce their activity.

Percutaneous spinal cord stimulation protocols often involve periodic stimulation sessions. As such, once the wire has been inserted into the subject's epidural cavity, a physician will often secure the wire in place by suturing the wire to the subject's skin and securing the wire to the subject's back (e.g., skin) with surgical tape. However, using a suture and surgical tape in this way to secure the wire against the subject's back has disadvantages. For example, when the subject sits down on a chair, the surgical tape might be the only barrier between the puncture wound in the subject's back and the chair. If the subject moves his or her back against the chair, the wire may be tugged out of the puncture wound or against the suture, causing pain or removing the wire from its effective location within the epidural space. That is, the surgical tape might not effectively isolate the puncture wound or hold the inserted wire in place when that area is impacted with moderate amounts of force.

SUMMARY

Within examples, a wire clamping device includes a base. The base includes an indentation, a first attachment component at a first end of the base, and a second attachment component at a second end of the base that is opposite the first end. The wire clamping device further includes an arm that includes a protrusion and a third attachment component that is attached to the first attachment component. The arm is configured to rotate with respect to the first attachment component to a position at which the arm is restrained by the second attachment component against the base and at least a portion of the protrusion is within the indentation or aligned with the indentation.

In another example, a tool for opening the wire clamping device includes a handle that includes a rounded surface and a protrusion that is substantially perpendicular to the handle. The rounded surface of the handle is configured to be on top of the second attachment component when the protrusion of the tool is underneath the extension of the arm.

In yet another example, a method for using the wire clamping device includes placing a wire over an indentation in an interior surface of a base of the device. An arm of the device is attached to the base at a first end of the base and configured to rotate with respect to the base. The method further includes rotating the arm toward the indentation. The method further includes securing the arm to the base at a second end of the base via an attachment component of the base, thereby restraining the arm against the base and pressing, via a protrusion of the arm, a portion of the wire into the indentation to restrain the wire between the protrusion and the indentation. The method further includes attaching, to a subject, an exterior surface of the base that is opposite the interior surface.

In yet another example, a method for using the opening tool to open the wire clamping device includes placing the protrusion of the tool under the extension of the arm and placing the rounded surface of the handle on top of the second attachment component. The method further includes moving the handle such that the rounded surface moves over the second attachment component and the protrusion of the tool pulls on the extension of the arm, thereby causing the second attachment component to release the arm.

These, as well as other aspects, advantages, and alternatives will become apparent to those of ordinary skill in the art by reading the following detailed description, with reference where appropriate to the accompanying drawings. Further, it should be understood that this summary and other descriptions and figures provided herein are intended to illustrate the invention by way of example only and, as such, that numerous variations are possible.

DETAILED DESCRIPTION

As discussed above, current methods for securing a percutaneously inserted wire have disadvantages. Accordingly, one aspect of the disclosure is a wire clamping device that includes a base. The base includes an indentation, a first attachment component at a first end of the base, and a second attachment component at a second end of the base that is opposite the first end. The wire clamping device further includes an arm that includes a protrusion and a third attachment component that is attached to the first attachment component. The arm is configured to rotate with respect to the first attachment component to a position at which the arm is restrained by the second attachment component against the base and at least a portion of the protrusion is within the indentation or aligned with the indentation.

Another aspect of the disclosure is a method for using the wire clamping device. In particular embodiments, a wire is inserted into the subject's epidural space through a puncture wound (e.g., on the subject's back). An exposed portion of the wire may be routed through a hole in the base and placed over the indentation in the interior surface of the base. The arm of the device may be rotated toward the indentation such that the arm is secured to the base at the second end of the base via the second attachment component of the base. This may cause the arm to be restrained against the base and the protrusion of the arm to press a portion of the wire into the indentation to restrain the wire between the protrusion and the indentation. Additionally, an exterior (e.g., back) surface of the base that is opposite the interior surface of the base may be attached to the subject (e.g., via an adhesive material). The device may be attached to the subject such that the hole is approximately centered above the puncture wound (e.g., near the insertion point of the wire). This may protect the puncture wound and secure the wire in place.

As such, using the wire clamping device may render it unnecessary for a physician to suture the wire to the subject's back, thereby perhaps reducing the subject's infection risk and discomfort. Using the wire clamping device may also reduce the amount of time the physician needs to complete the procedure. The wire clamping device may also be more effective at preventing migration of the wire and/or protecting the puncture wound than suturing the wire to skin and/or using surgical tape.

Figure 1:
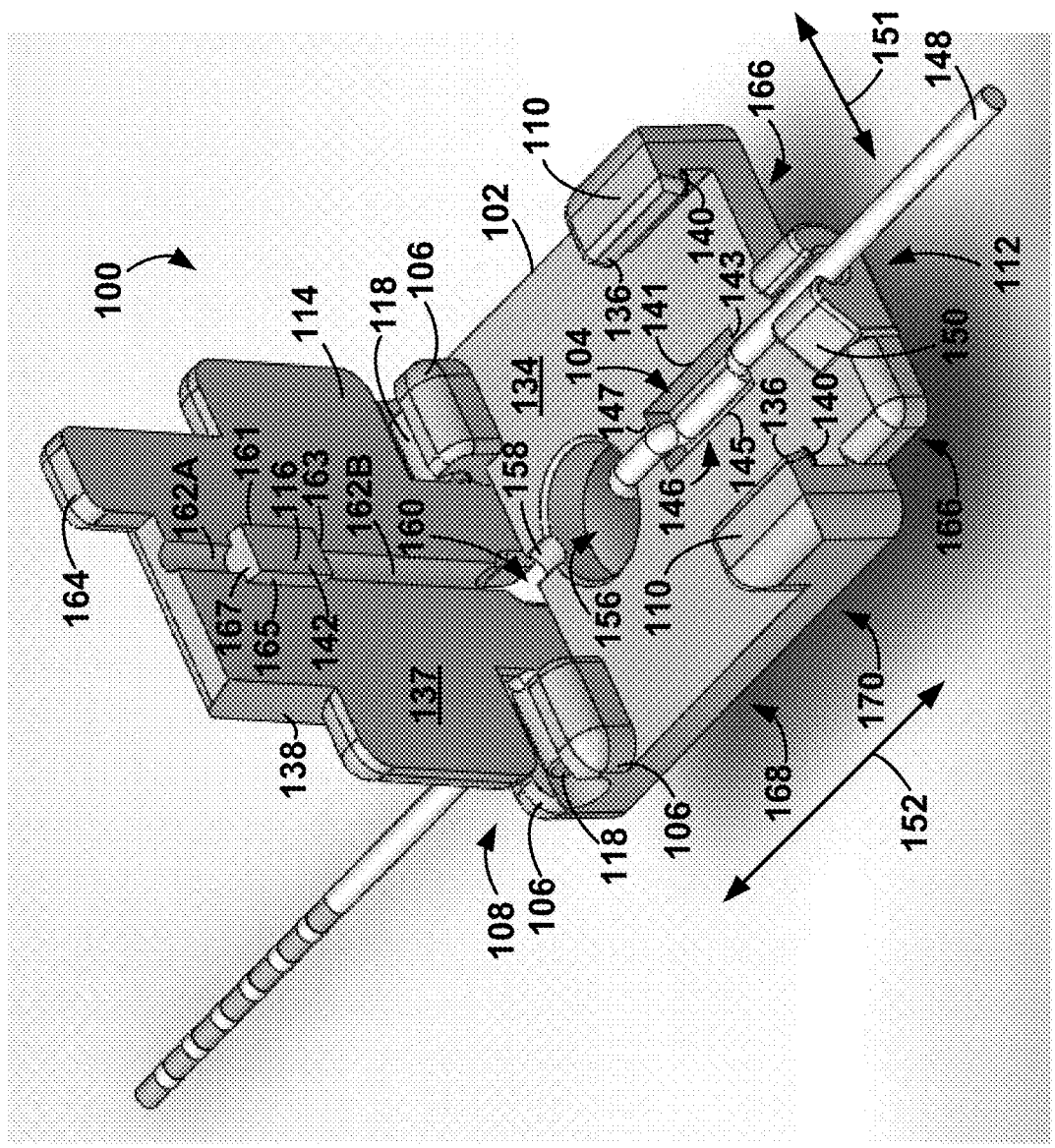
FIG. 1 is a perspective view of a wire clamping device in an open state, according to an embodiment of the disclosure.

FIG. 1 is a perspective view of a wire clamping device 100 (also referred to herein as the device 100) in an open state. The wire clamping device 100 includes a base 102 that includes an indentation 104 (e.g., on an interior surface 134 of the base 102), an attachment component 106 at an end 108 of the base 102, and an attachment component 110 at an end 112 of the base 102 that is opposite the end 108. The device 100 further includes an arm 114 that includes a protrusion 116 and an attachment component 118 that is attached (e.g., rotatably attached) to the attachment component 106. The arm 114 is configured to rotate with respect to the attachment component 106 to a position at which the arm 114 is restrained by the attachment component 110 against the base 102 and at least a portion of the protrusion 116 is within the indentation 104 or aligned with the indentation 104 (see FIGS. 7, 8, 9, 14, and 15). More specifically, the arm 114 is configured to move underneath extensions 140 of the attachment component 110 to be restrained by the attachment component 110 against the base 102.

The base 102 and the arm 114 may be formed of plastic and/or metal, but other materials are possible. As shown, the attachment component 118 snaps into the attachment component 106 to form a hinged connection. That is, the arm 114 and the attachment component 118 may rotate with respect to the attachment component 106.

The base 102 further includes a wire guide 150 at the end 112 of the base. The wire guide 150 is configured to receive a wire 148 (e.g., an electrically conductive wire). The wire guide 150 is configured to resist motion of the wire 148 in a direction 151 that is parallel with an axis of rotation of the arm (e.g., the attachment component 118). The wire guide 150 is also configured to resist motion of the wire 148 in a direction 152 that is perpendicular with an axis of rotation of the arm. For example, the wire guide 150 is configured to clasp the wire 148.

The base 102 further includes a hole 156 between the indentation 104 and the end 108 of the base 102. The base 102 also includes a groove 158 at the end 108 that is configured to receive the wire 148 (see FIG. 2).

The arm 114 also includes a notch 160 adjacent to the groove 158. The notch 160 is configured to receive the wire 148 (see FIG. 2). The arm 114 further includes a portion 162A and a portion 162B of a groove that is configured to receive the wire 148 (see FIG. 7). The portion 162A and the portion 162B are on opposite sides of the protrusion 116. The protrusion 116 is configured to press a portion 146 of the wire 148 into the indentation 104. The portion 162A and the portion 162B of the groove are configured to resist motion of the wire 148 in a direction 151 that is parallel to an axis of rotation of the arm (see FIG. 7). The protrusion 116 is wider than the portions of the groove 162A and 162B in the direction 151 as shown in FIG. 1. The protrusion 116 has a rectangular face 142, but other examples are possible.

The arm 114 is configured to rotate with respect to the attachment component 106 to a position at which no portion of the protrusion 116 extends beyond any boundary of the indentation 104 in any direction parallel to the interior surface 134 of the base 102 (e.g, the directions 151 and 152). For example, when the device 100 is "closed," the boundaries 161, 163, 165, and 167 respectively do not extend beyond the boundaries 141, 143, 145, and 147 of the indentation 104.

Figure 7:
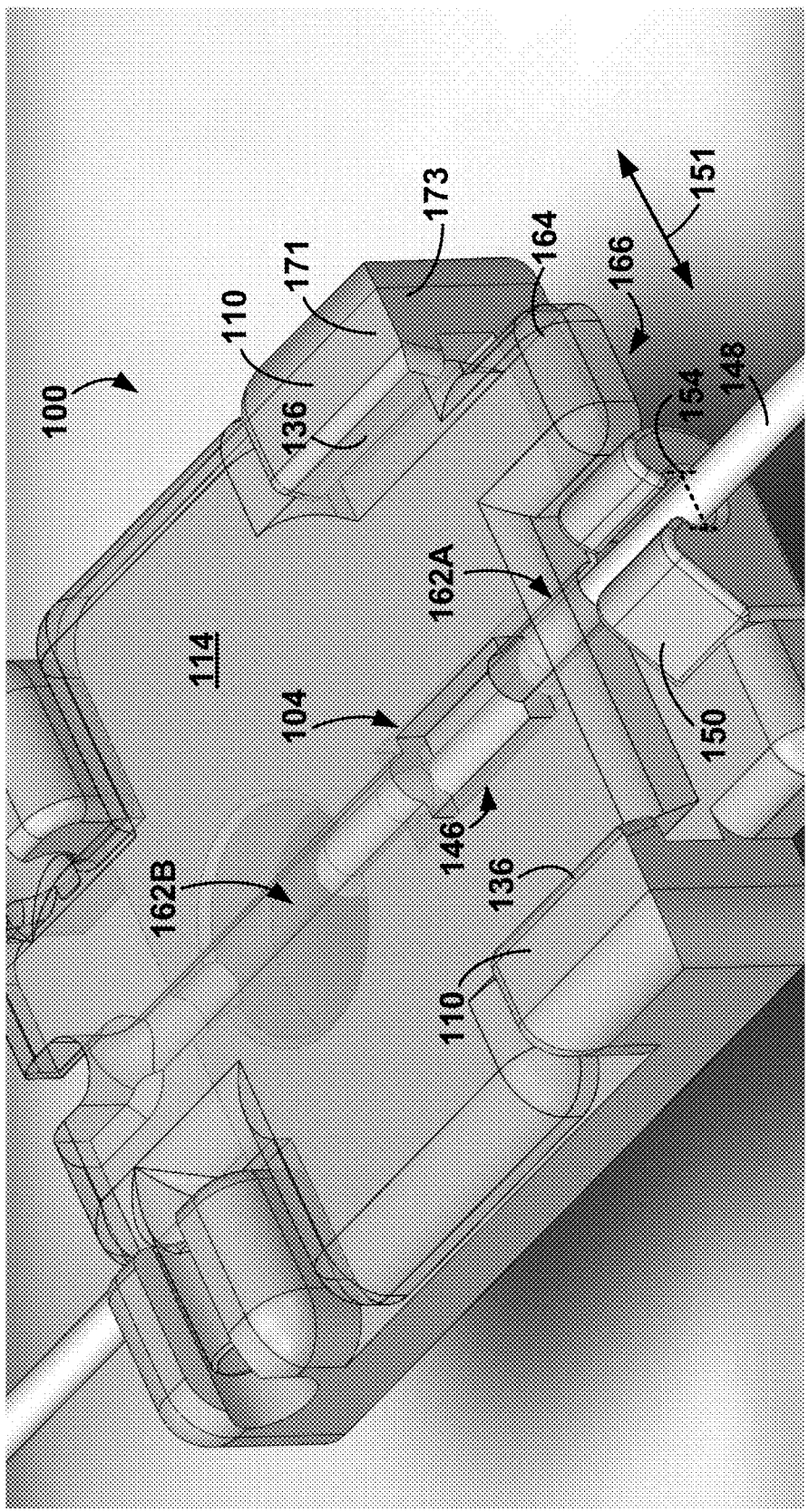
FIG. 7 is a partially transparent perspective view of a wire clamping device in a closed state, according to an embodiment of the disclosure.
Figure 18:
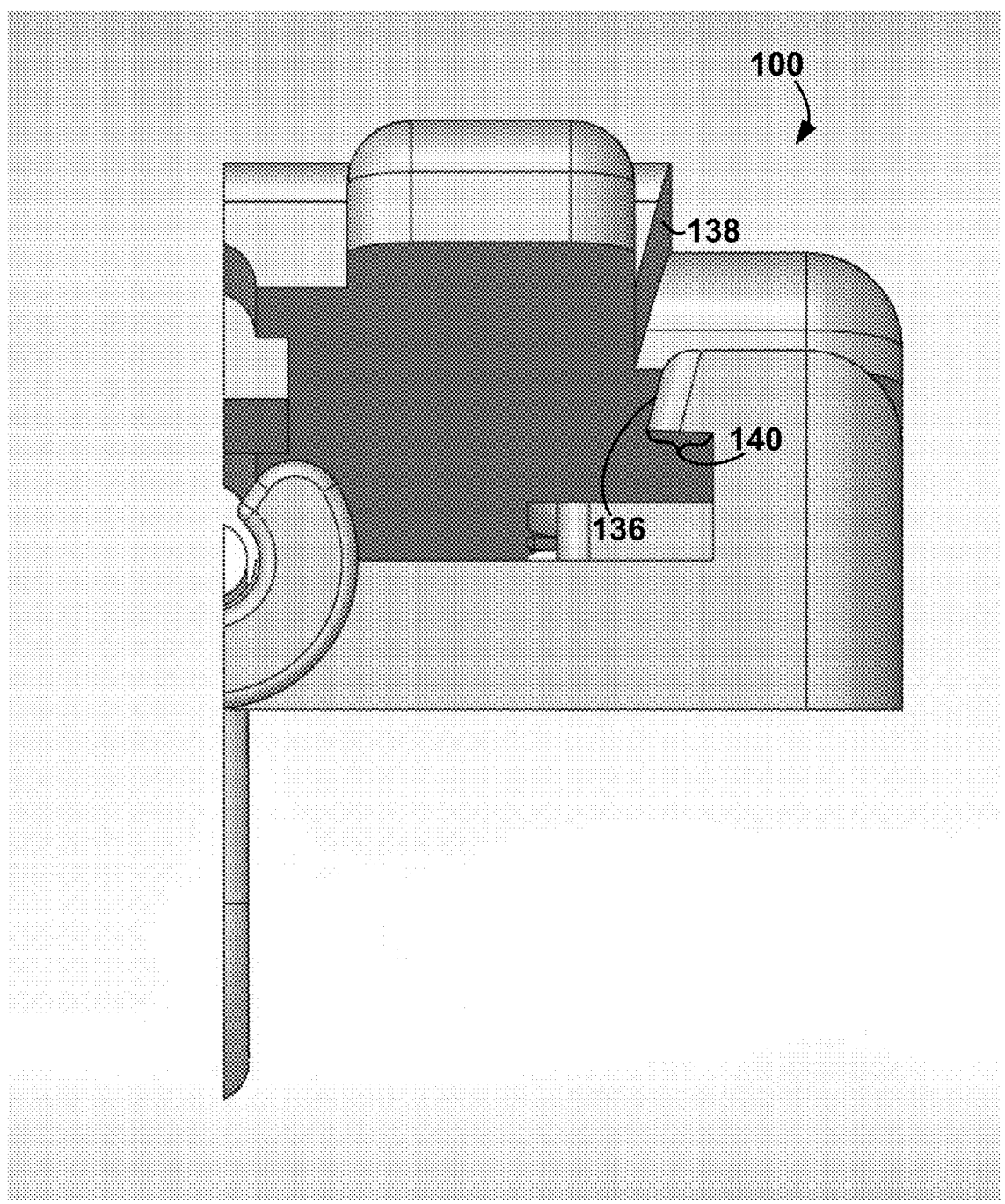
FIG. 18 is a partial front view of a wire clamping device in an open state, according to an embodiment of the disclosure.
Figure 19:
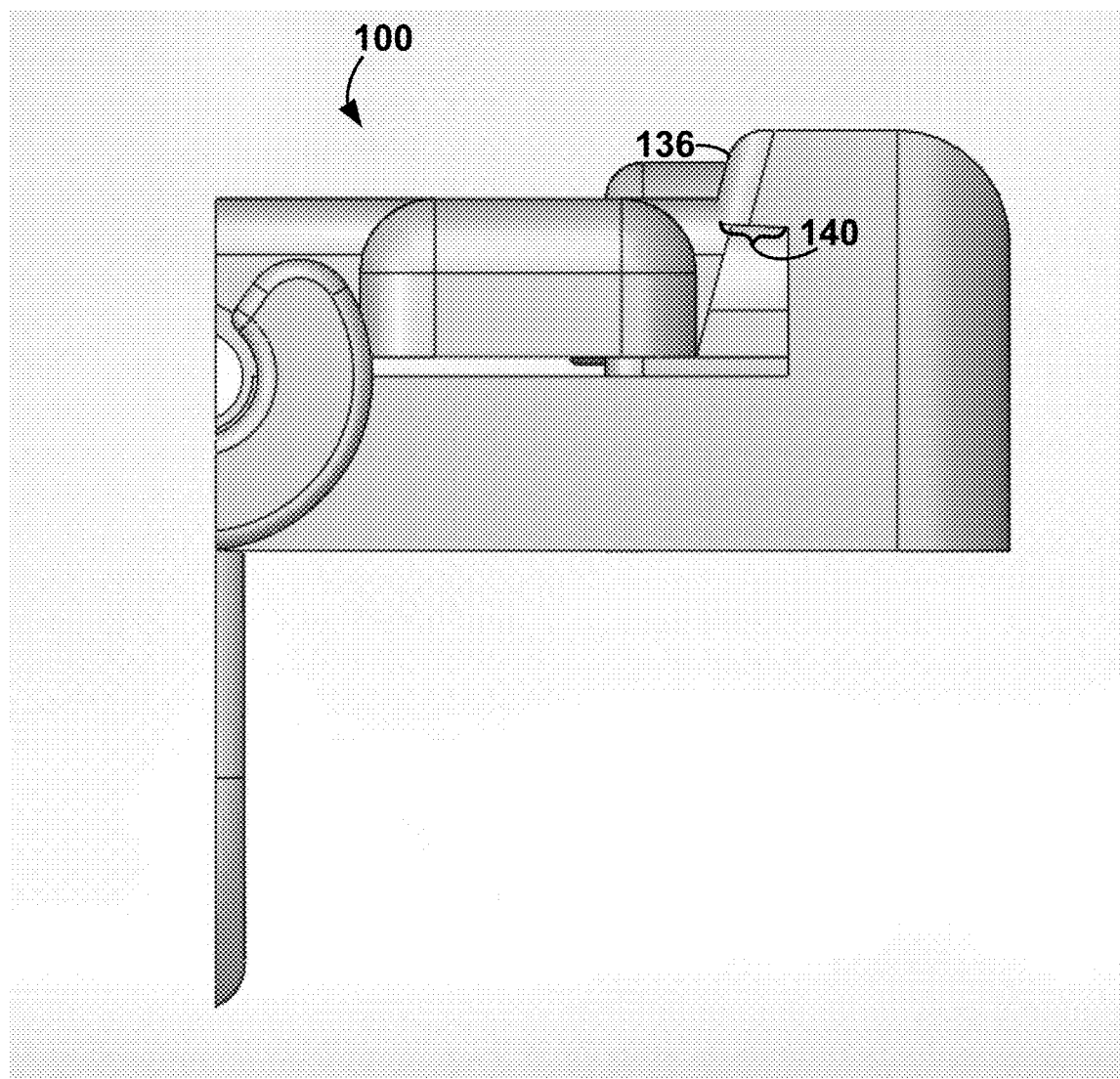
FIG. 19 is a partial front view of a wire clamping device in a closed state, according to an embodiment of the disclosure.

The attachment component 110 comprises surfaces 136 that are sloped with respect to the interior surface 134 (see FIGS. 7, 18, and 19). The arm 114 also includes surfaces 138 (see FIGS. 11 and 18) that are sloped with respect to the interior surface 134 and are configured to move against the surfaces 136 as the arm 114 is rotated toward the base 102. Additionally, the attachment component 110 includes extensions 140 configured to protrude over the arm 114 to restrain the arm 114 against the base 102 (see FIG. 19).

Figure 2:
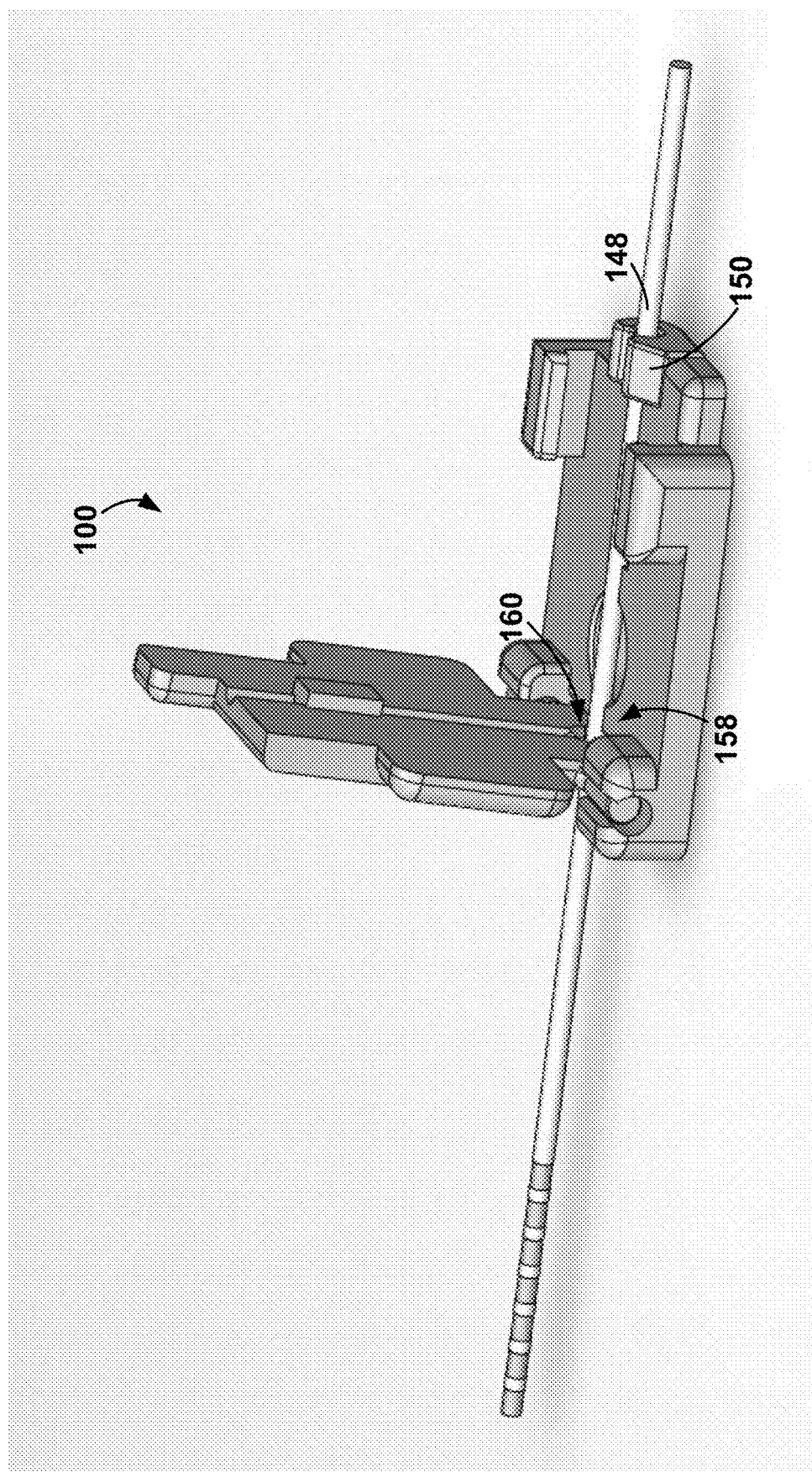
FIG. 2 is a side view of a wire clamping device in an open state, according to an embodiment of the disclosure.

FIG. 2 is a side view of the wire clamping device 100 in an open state. In FIG. 2, the wire 148 is inserted through the wire guide 150, the groove 158, and the notch 160.

Figure 3:
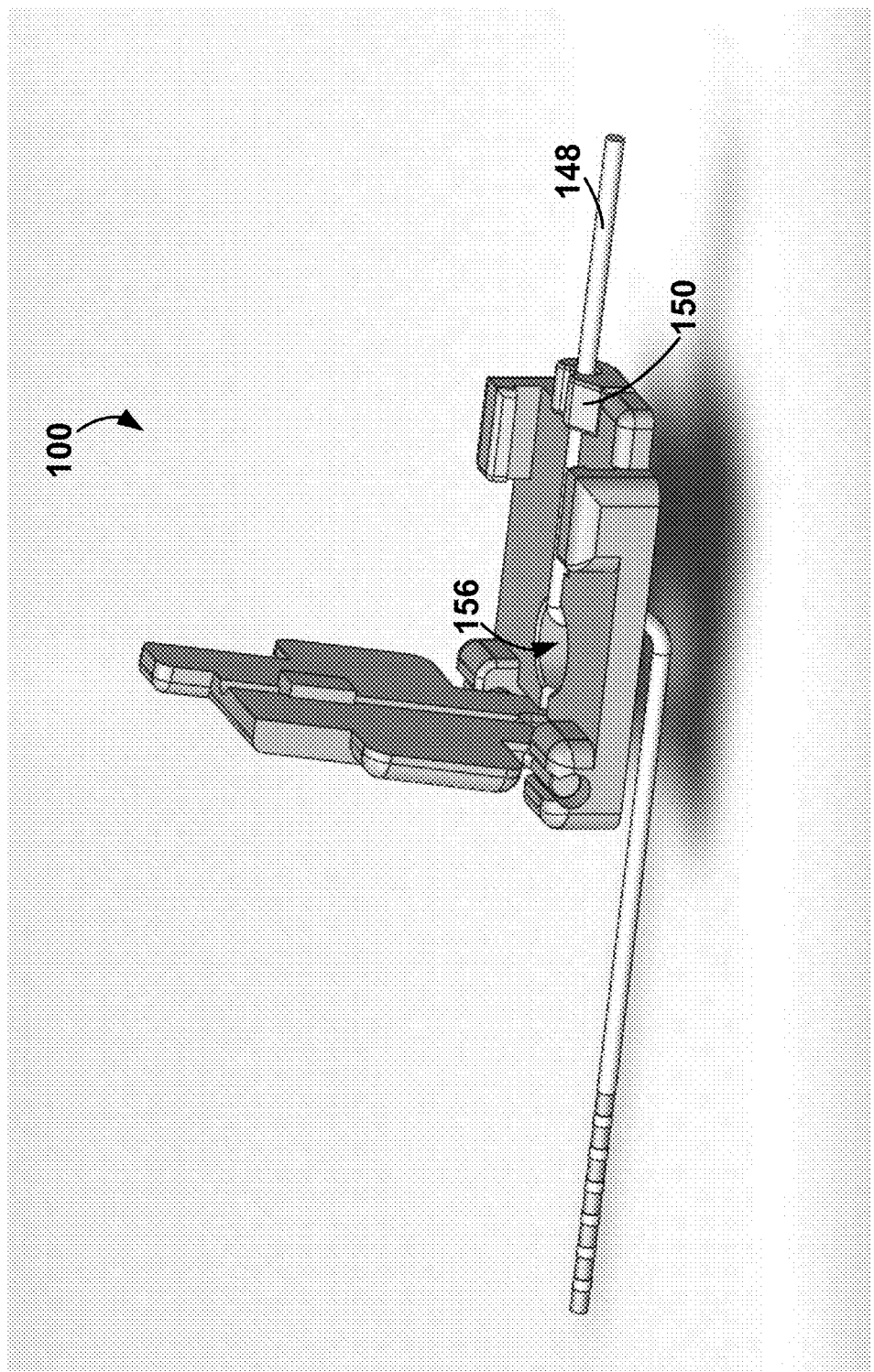
FIG. 3 is a side view of a wire clamping device in an open state, according to an embodiment of the disclosure.

FIG. 3 is also a side view of the wire clamping device 100 in an open state. However, in FIG. 3 the wire 148 is inserted through the wire guide 150 and the hole 156.

Figure 4:
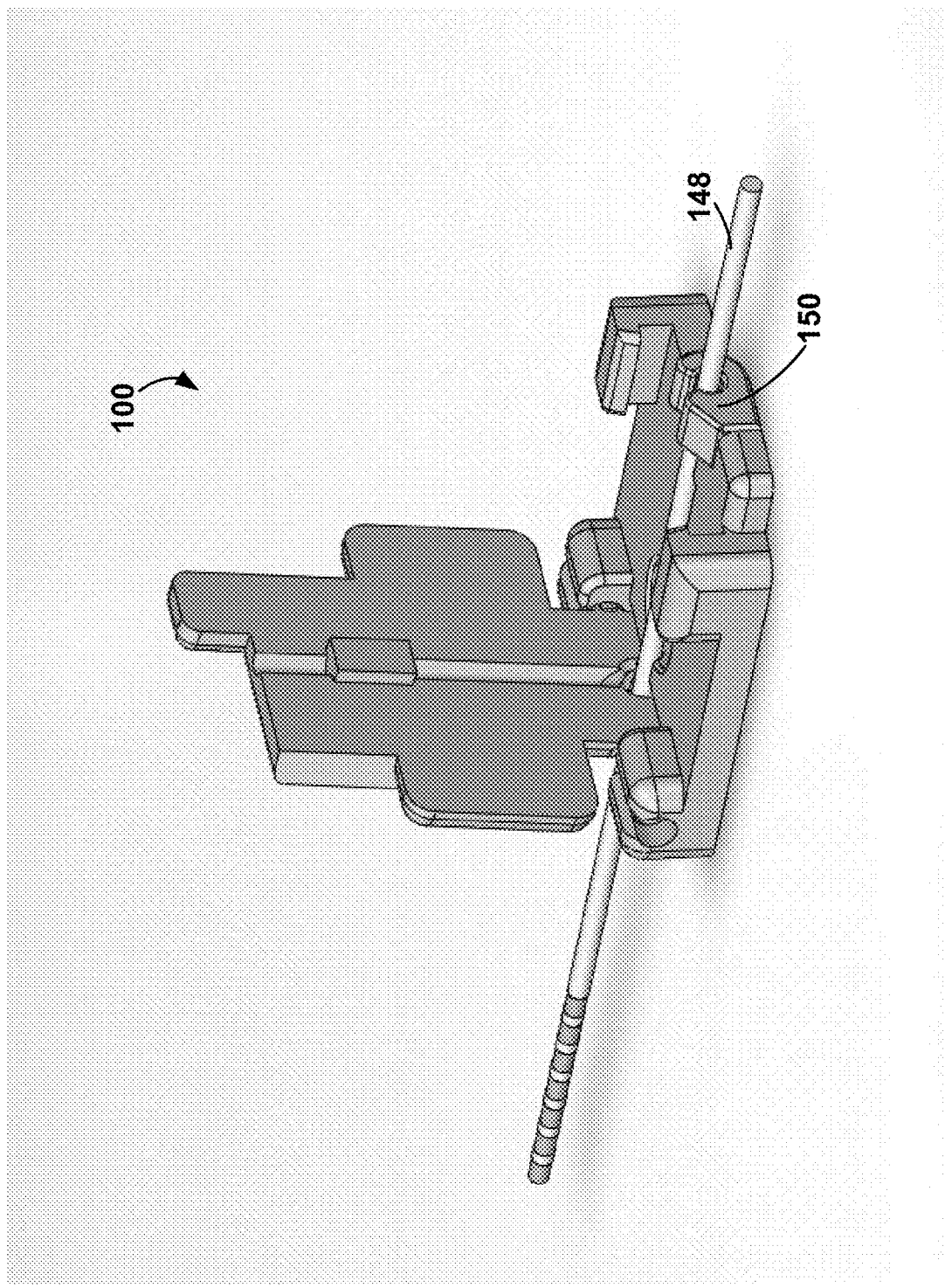
FIG. 4 is a perspective view of a wire clamping device in an open state, according to an embodiment of the disclosure.

FIG. 4 is a perspective view of the wire clamping device 100 in an open state.

Figure 5:
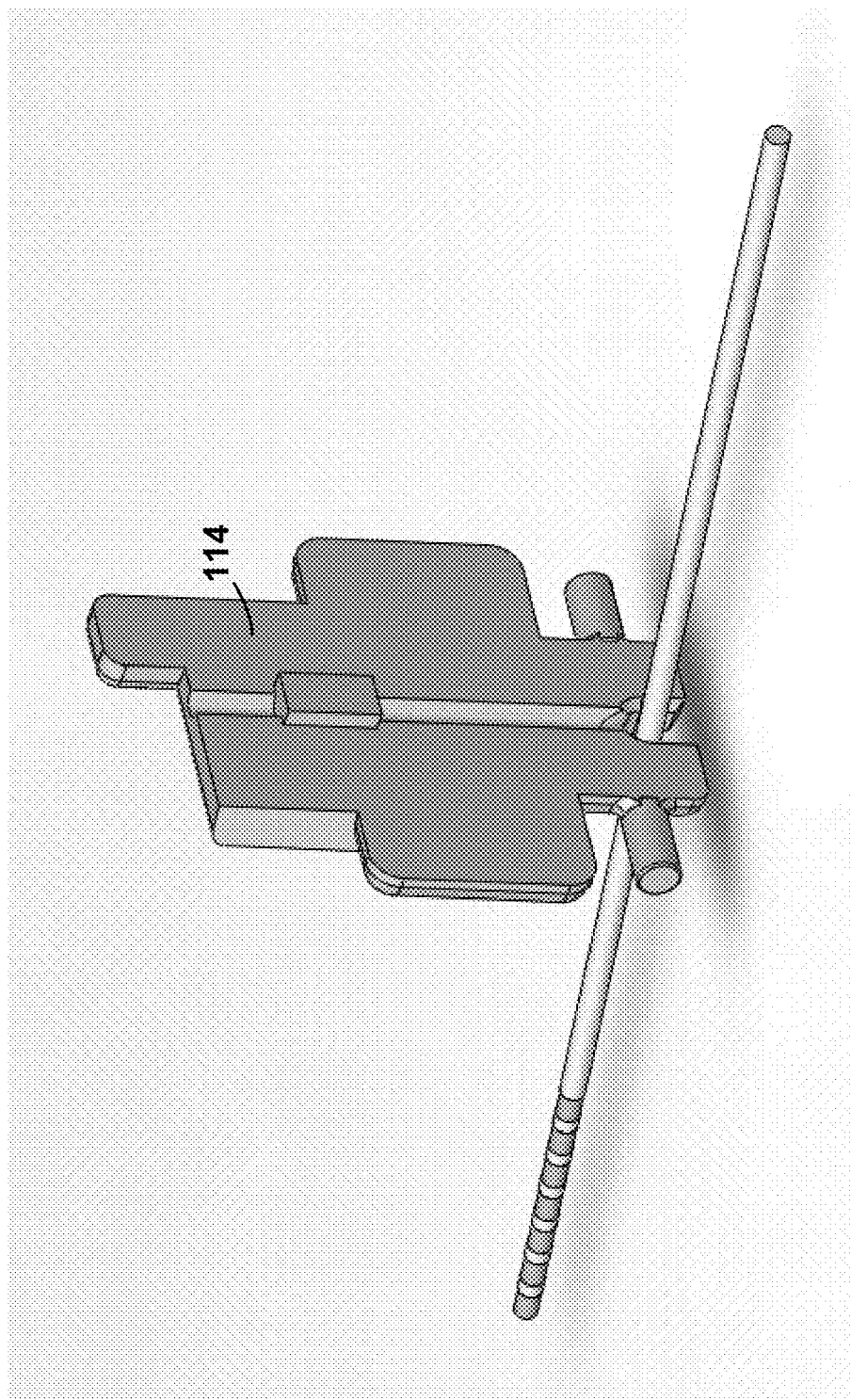
FIG. 5 is an isolated view of an arm of a wire clamping device, according to an embodiment of the disclosure.

FIG. 5 is an isolated view of the arm 114 of the wire clamping device 100.

Figure 6:
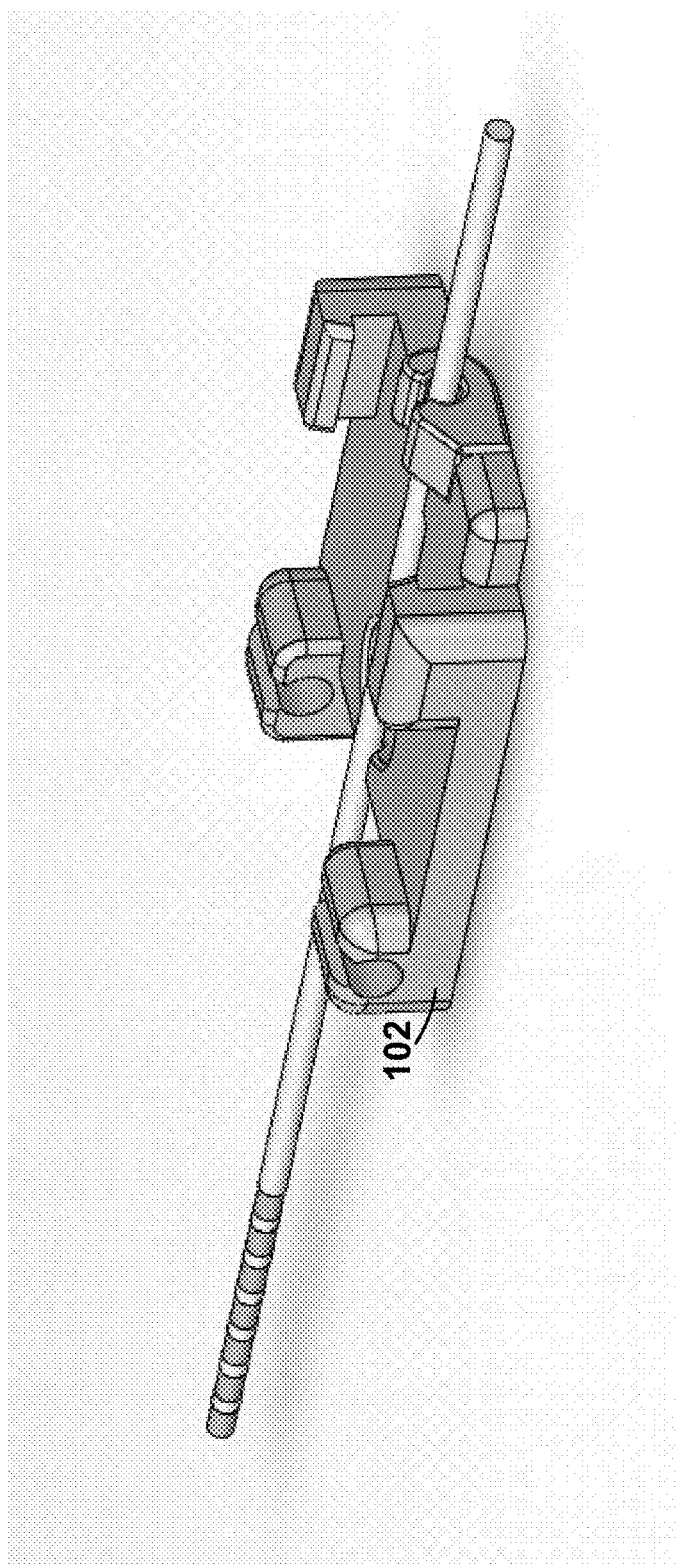
FIG. 6 is an isolated view of a base of a wire clamping device, according to an embodiment of the disclosure.

FIG. 6 is an isolated view of the base 102 of the wire clamping device 100.

FIG. 7 is a partially transparent perspective view of the wire clamping device 100 in a closed state. In the closed state, the device 100 may restrain the portion 146 of the wire 148 within the indentation 104. The wire guide 150 may have an inner diameter 154 within a range of 0.5 millimeters (mm) to 1.5 mm, 0.75 mm to 1.25 mm, or 0.95 mm to 1.05 mm. Additionally, the arm 114 includes an extension 164 that is configured to protrude past a portion 166 (see FIG. 1) of the base 102 adjacent to the end 112 of the base 102 when the arm 114 is restrained by the attachment component 110.

Figure 8:
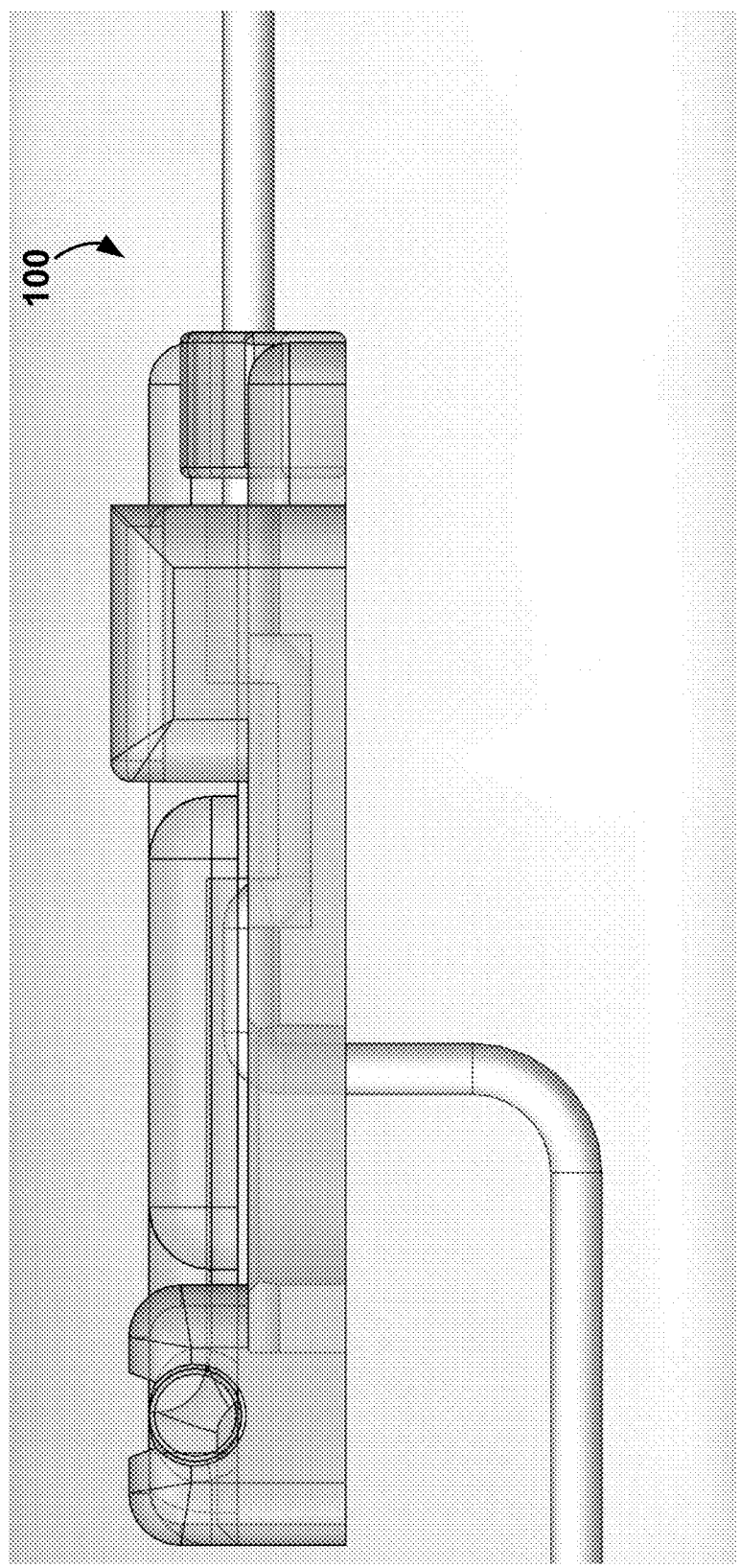
FIG. 8 is a partially transparent side view of a wire clamping device in a closed state, according to an embodiment of the disclosure.

FIG. 8 is a partially transparent side view of the wire clamping device 100 in a closed state.

Figure 9:
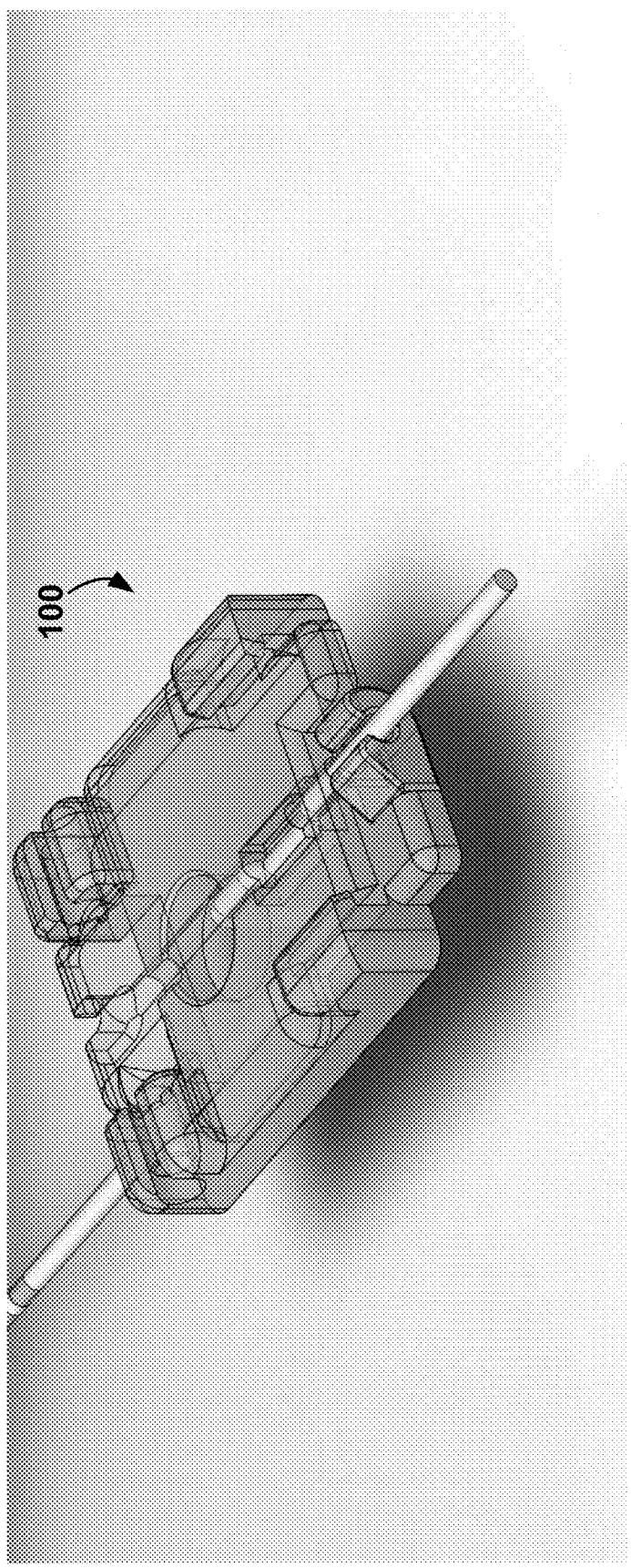
FIG. 9 is a partially transparent perspective view of a wire clamping device in a closed state, according to an embodiment of the disclosure.

FIG. 9 is a partially transparent perspective view of the wire clamping device 100 in a closed state.

Figure 10:
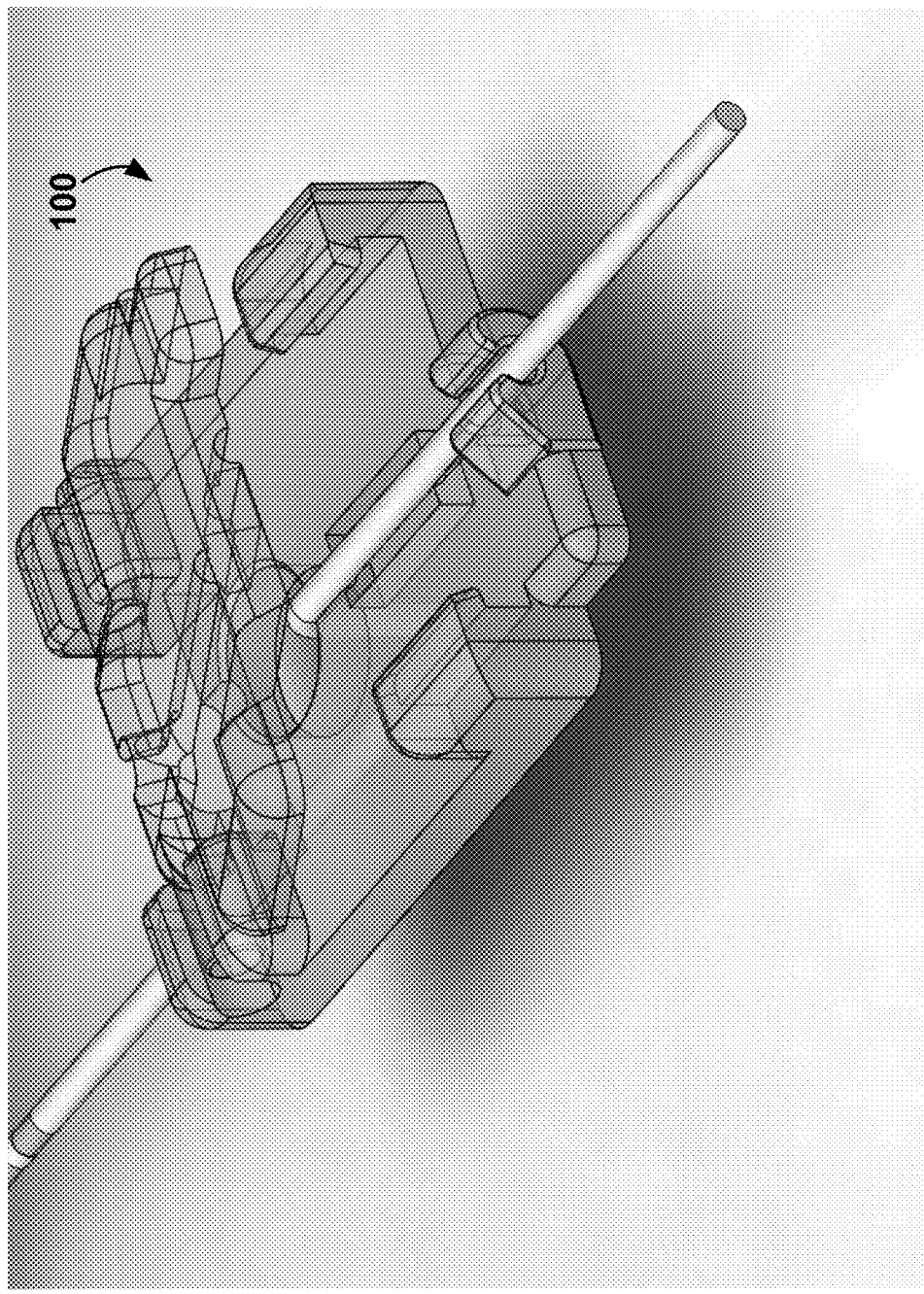
FIG. 10 is a partially transparent perspective view of a wire clamping device in an open state, according to an embodiment of the disclosure.

FIG. 10 is a partially transparent perspective view of the wire clamping device 100 in an open state.

Figure 11:
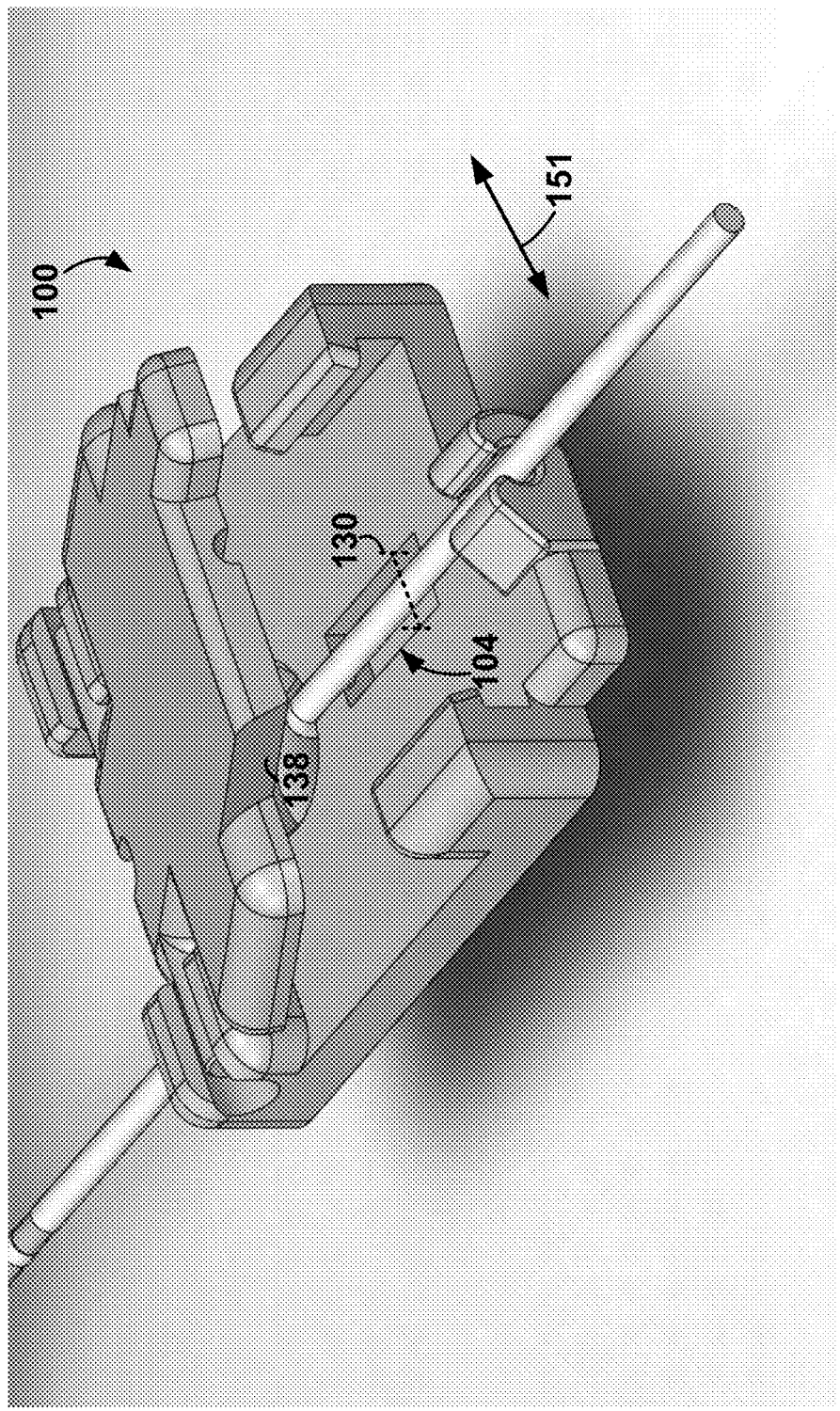
FIG. 11 is a perspective view of a wire clamping device in an open state, according to an embodiment of the disclosure.

FIG. 11 is a perspective view of the wire clamping device 100 in an open state. As shown, the indentation 104 has a width 130 along the direction 151 that is parallel to an axis of rotation of the arm. The width 130 may be within a range of 1.5 millimeters (mm) to 2.5 mm, 1.75 mm to 2.25 mm, or 1.95 mm to 2.05 mm.

Figure 12:
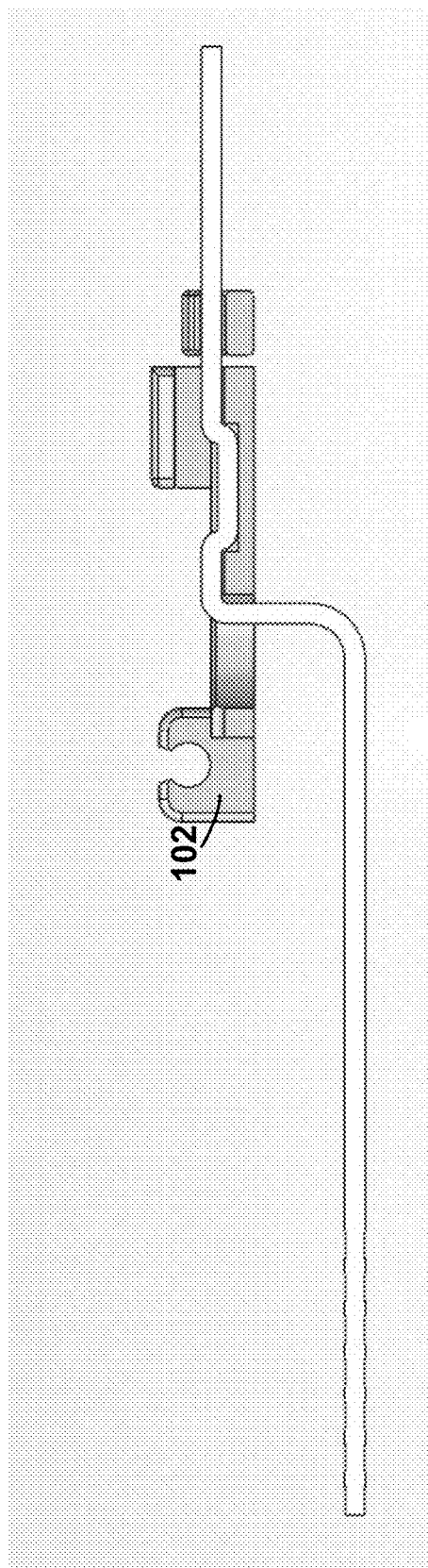
FIG. 12 is a cross sectional view of a base of a wire clamping device, according to an embodiment of the disclosure.

FIG. 12 is a cross sectional view of the base 102 of the wire clamping device 100.

Figure 13:
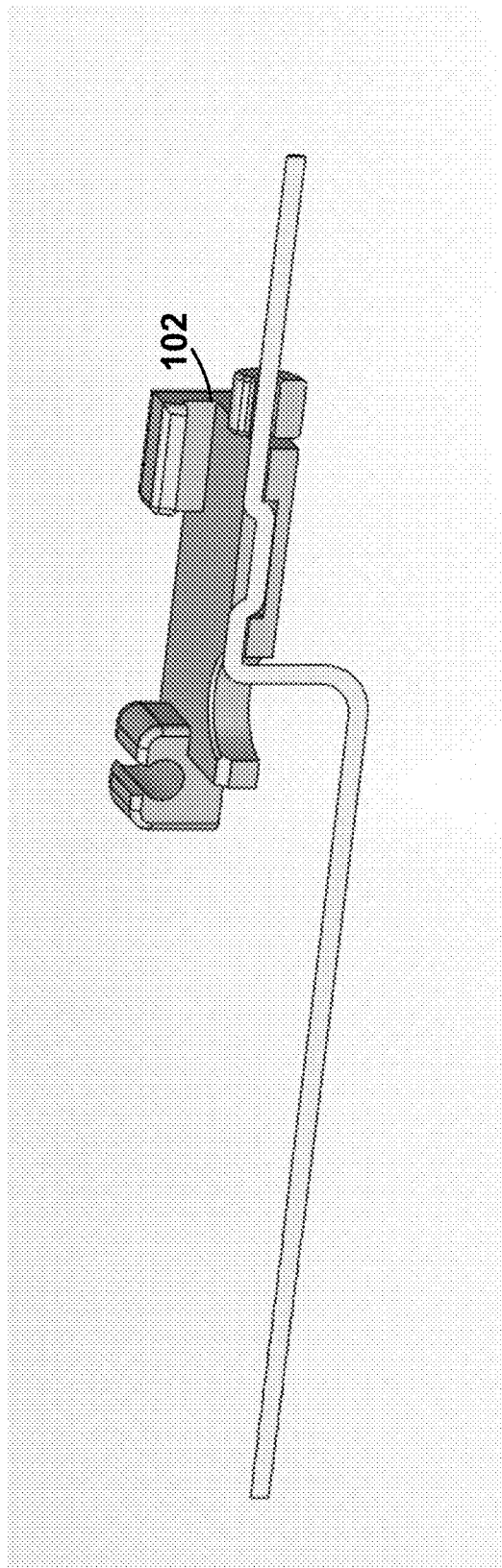
FIG. 13 is a cross sectional view of a base of a wire clamping device, according to an embodiment of the disclosure.

FIG. 13 is a cross sectional view of the base 102 of the wire clamping device 100.

Figure 14:
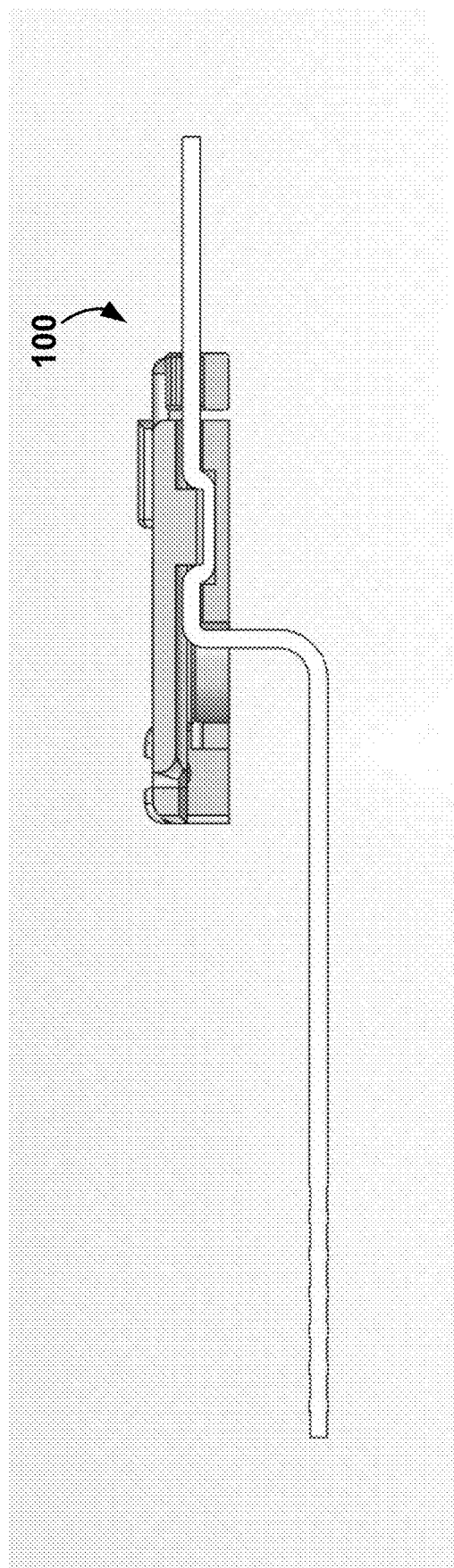
FIG. 14 is a cross sectional view of a wire clamping device in a closed state, according to an embodiment of the disclosure.

FIG. 14 is a cross sectional view of the wire clamping device 100 in a closed state.

Figure 15:
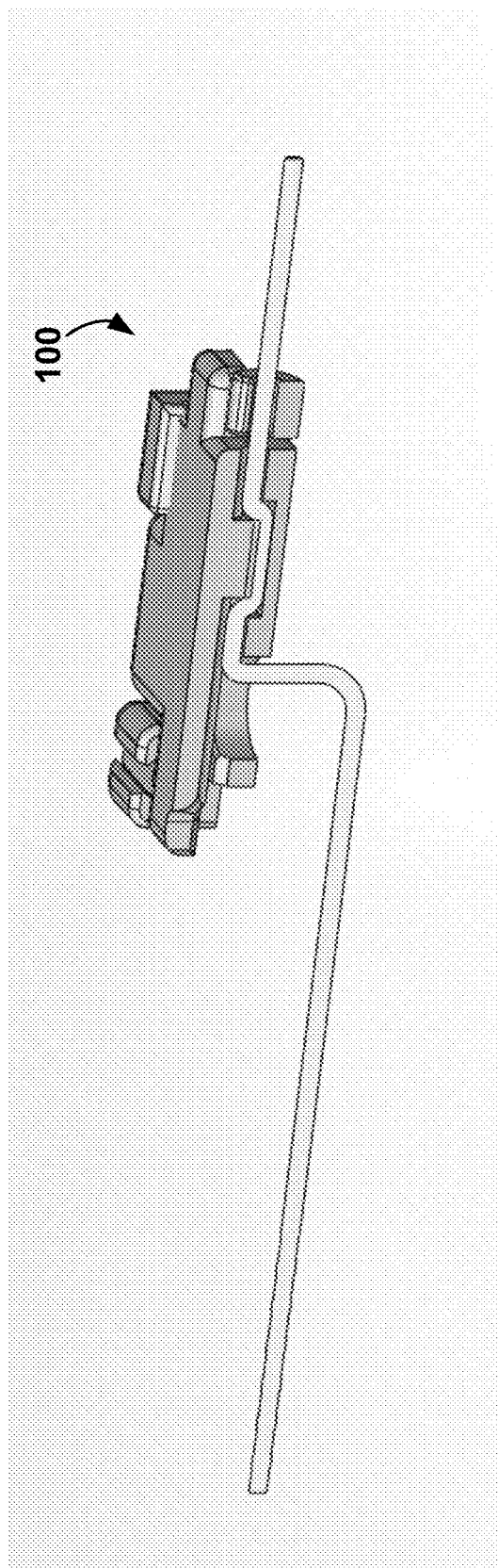
FIG. 15 is a cross sectional view of a wire clamping device in a closed state, according to an embodiment of the disclosure.

FIG. 15 is a cross sectional view of the wire clamping device 100 in a closed state.

Figure 16:
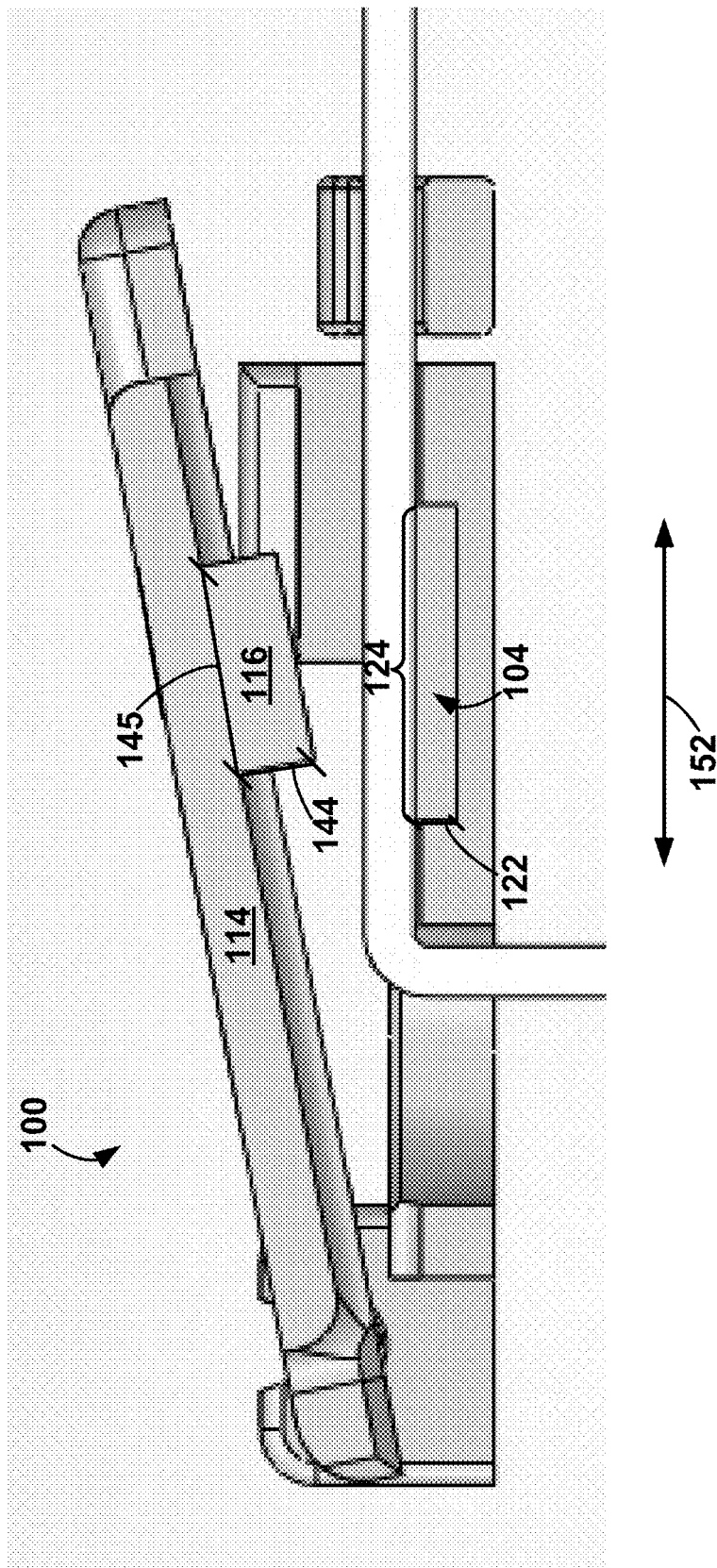
FIG. 16 is a cross sectional view of a wire clamping device in an open state, according to an embodiment of the disclosure.

FIG. 16 is a cross sectional view of the wire clamping device 100 in an open state. The indentation 104 may have a depth 122 within a range of 1.0 millimeters (mm) to 2.0 mm, 1.25 mm to 1.75 mm, or 1.45 mm to 1.55 mm. The indentation 104 may also have a length 124 along the direction 152 within a range of 4.5 millimeters (mm) to 5.5 mm, 4.75 mm to 5.25 mm, or 4.95 mm to 5.05 mm. The protrusion 116 may extend below the arm 114 at a depth 144 within a range of 0.4 mm to 1.4 mm, 0.65 mm to 1.15 mm, or 0.85 mm to 0.95 mm. The protrusion 116 may also have a length 145 along the direction 152 (when the device 100 is closed) that is within a range of 2.5 mm to 3.5 mm, 2.75 mm to 3.25 mm, or 2.95 mm to 3.05 mm.

Figure 17:
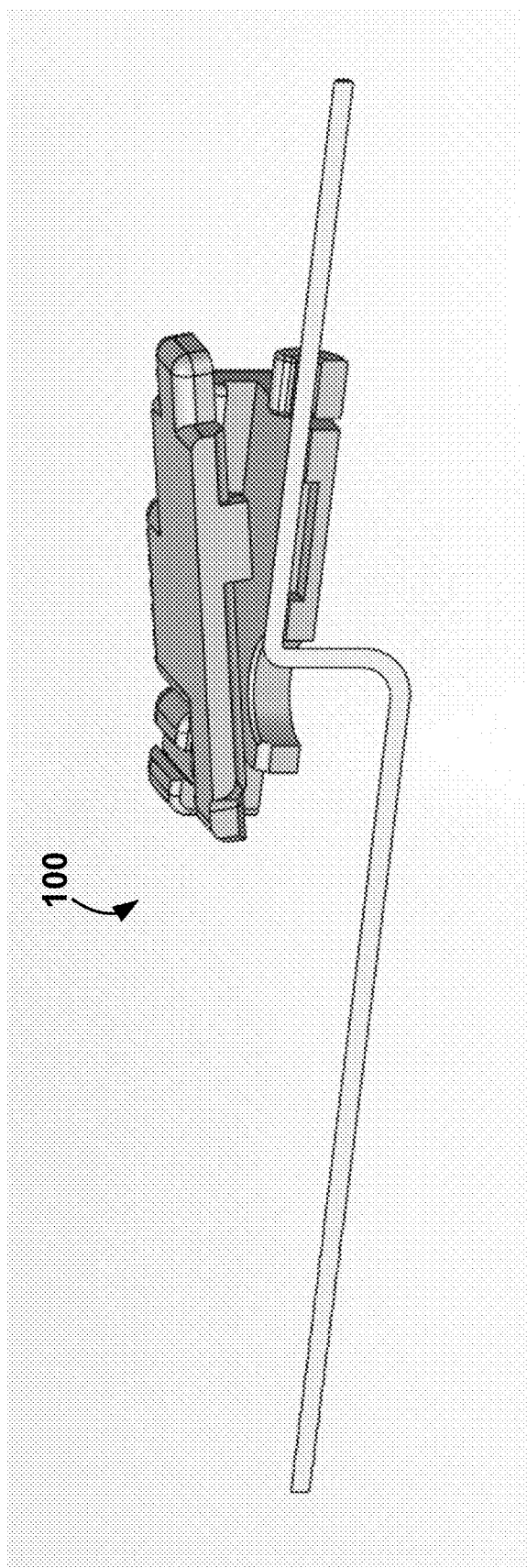
FIG. 17 is a cross sectional view of a wire clamping device in an open state, according to an embodiment of the disclosure.

FIG. 17 is a cross sectional view of the wire clamping device 100 in an open state.

FIG. 18 is a partial front view of the wire clamping device 100 in an open state.

FIG. 19 is a partial front view of the wire clamping device 100 in a closed state.

Figure 20:
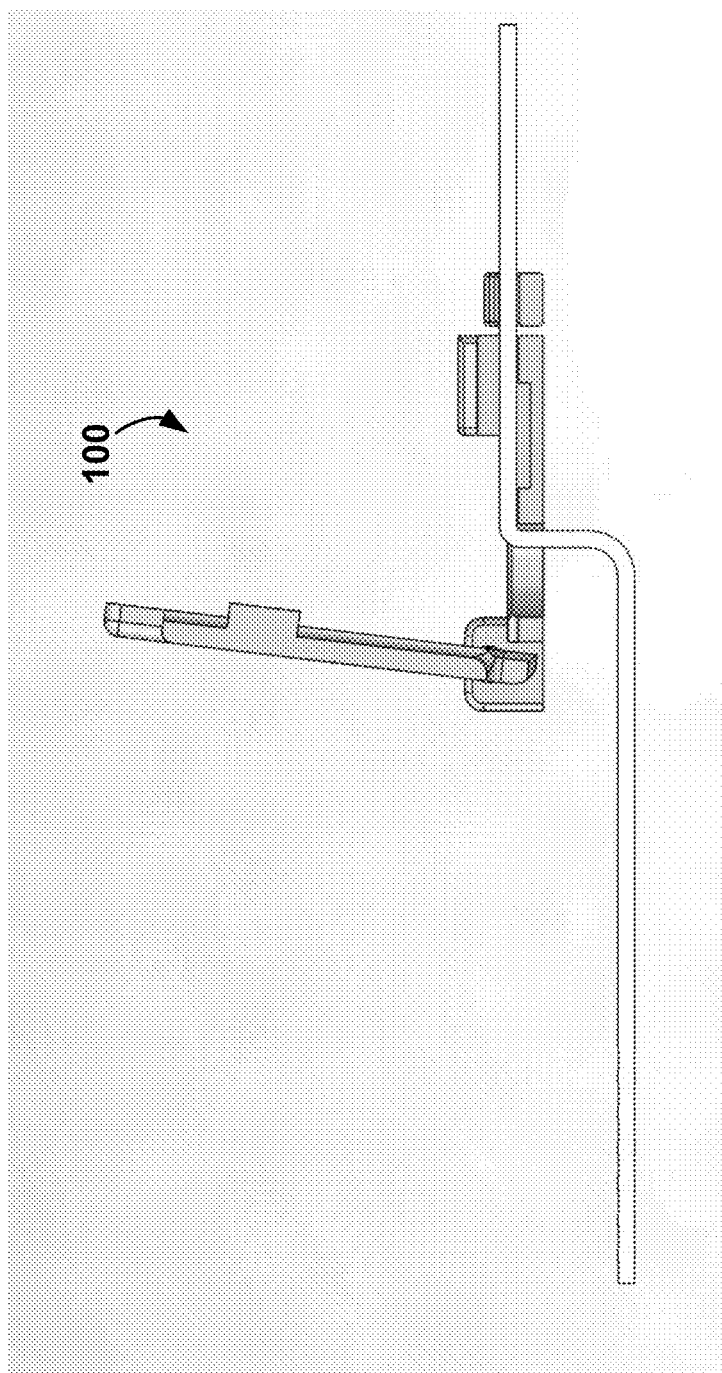
FIG. 20 is a cross sectional view of a wire clamping device in an open state, according to an embodiment of the disclosure.

FIG. 20 is a cross sectional view of the wire clamping device 100 in an open state.

Figure 21:
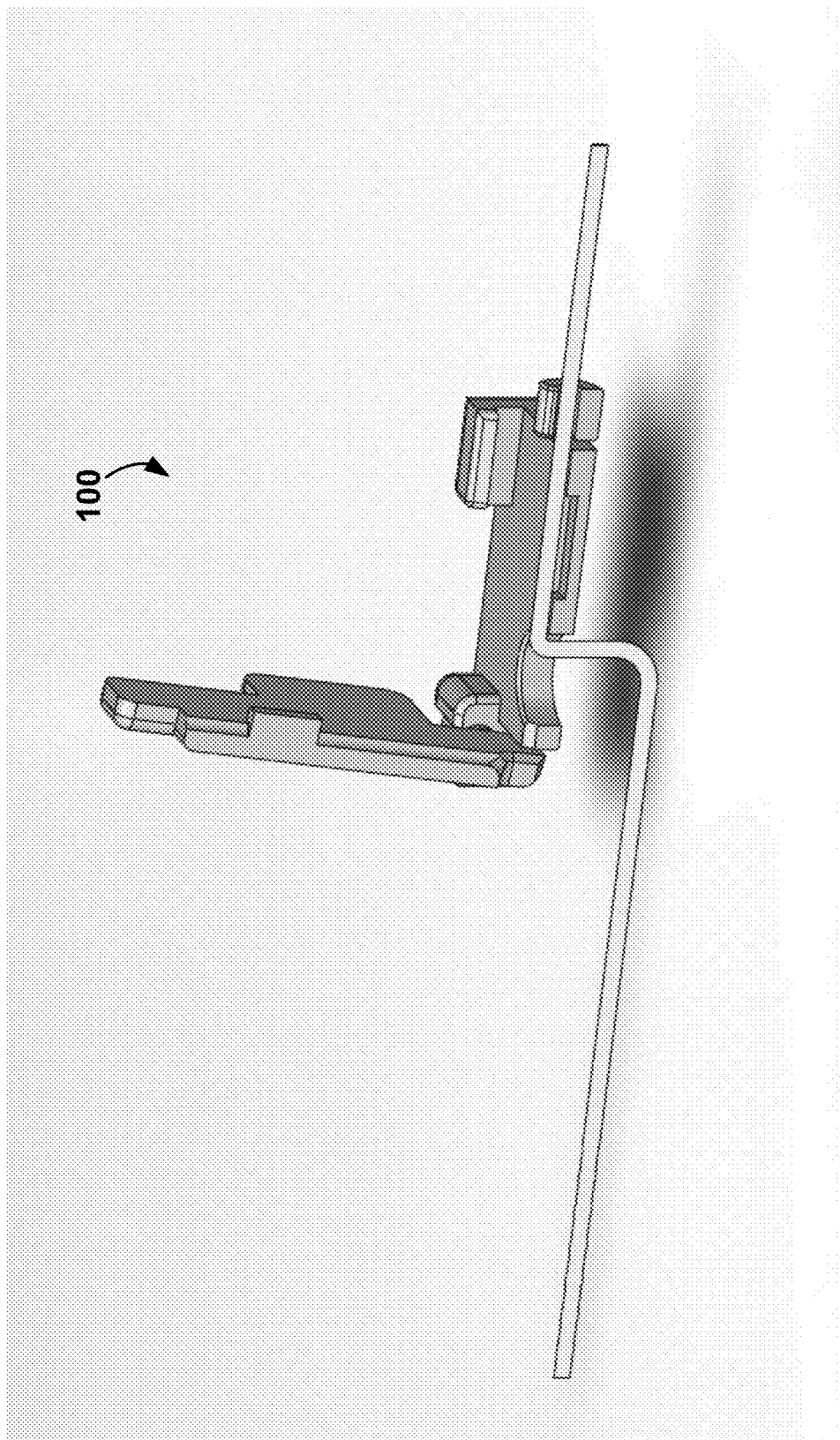
FIG. 21 is a cross sectional view of a wire clamping device in an open state, according to an embodiment of the disclosure.

FIG. 21 is a cross sectional view of the wire clamping device 100 in an open state.

Figure 22:
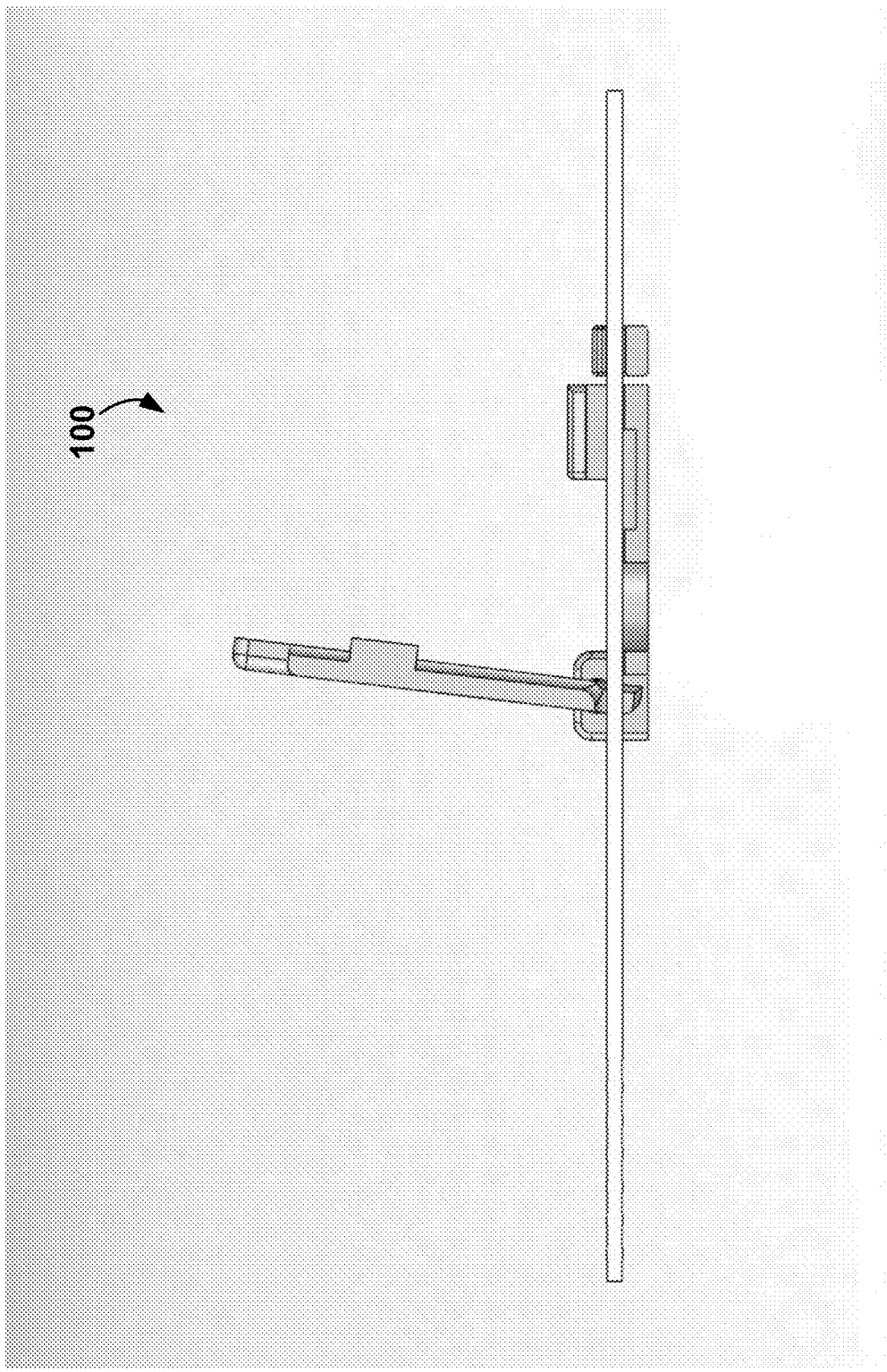
FIG. 22 is a cross sectional view of a wire clamping device in an open state, according to an embodiment of the disclosure.

FIG. 22 is a cross sectional view of the wire clamping device 100 in an open state.

Figure 23:
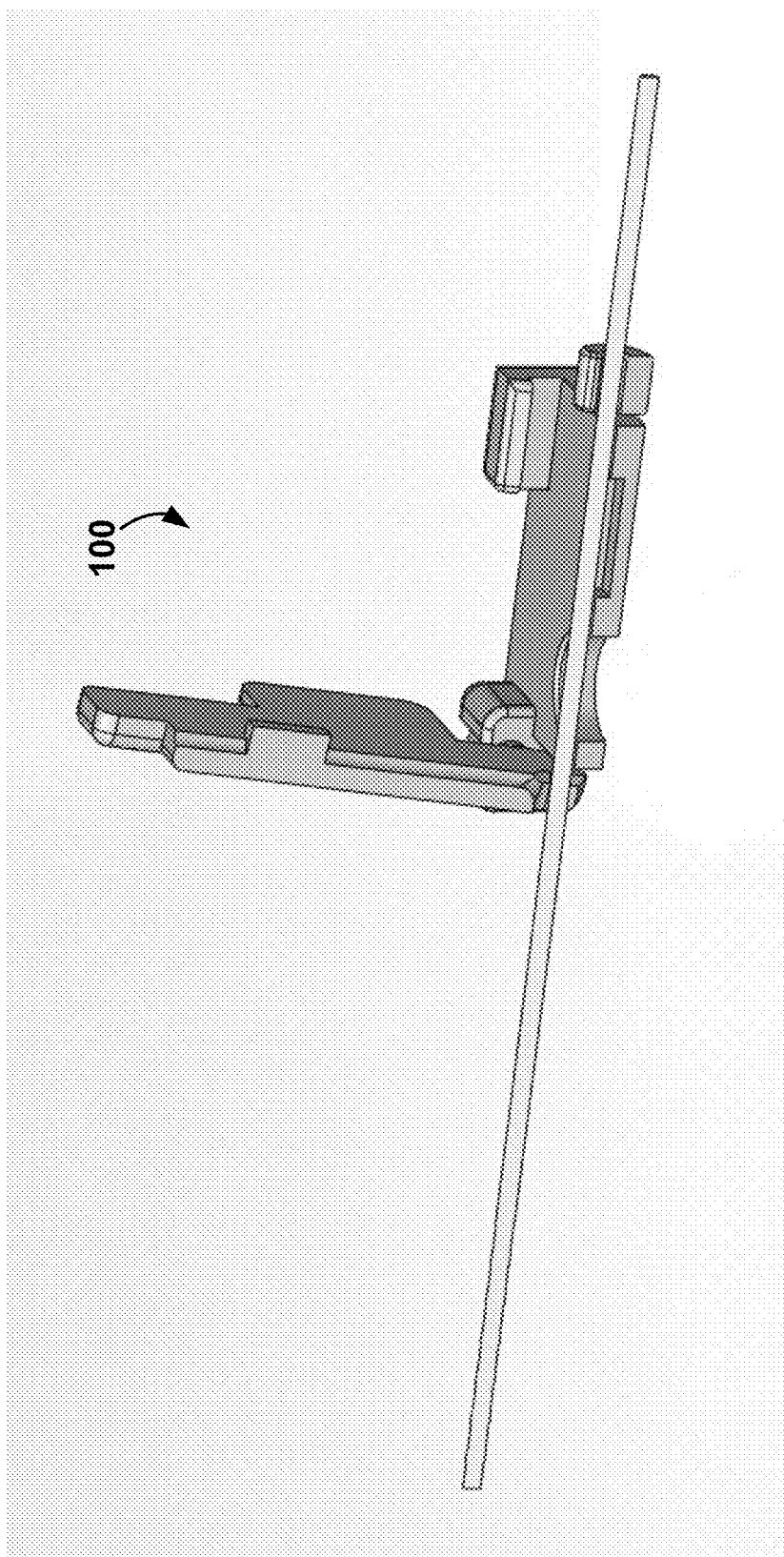
FIG. 23 is a cross sectional view of a wire clamping device in an open state, according to an embodiment of the disclosure.

FIG. 23 is a cross sectional view of the wire clamping device in an open state.

Figure 24:
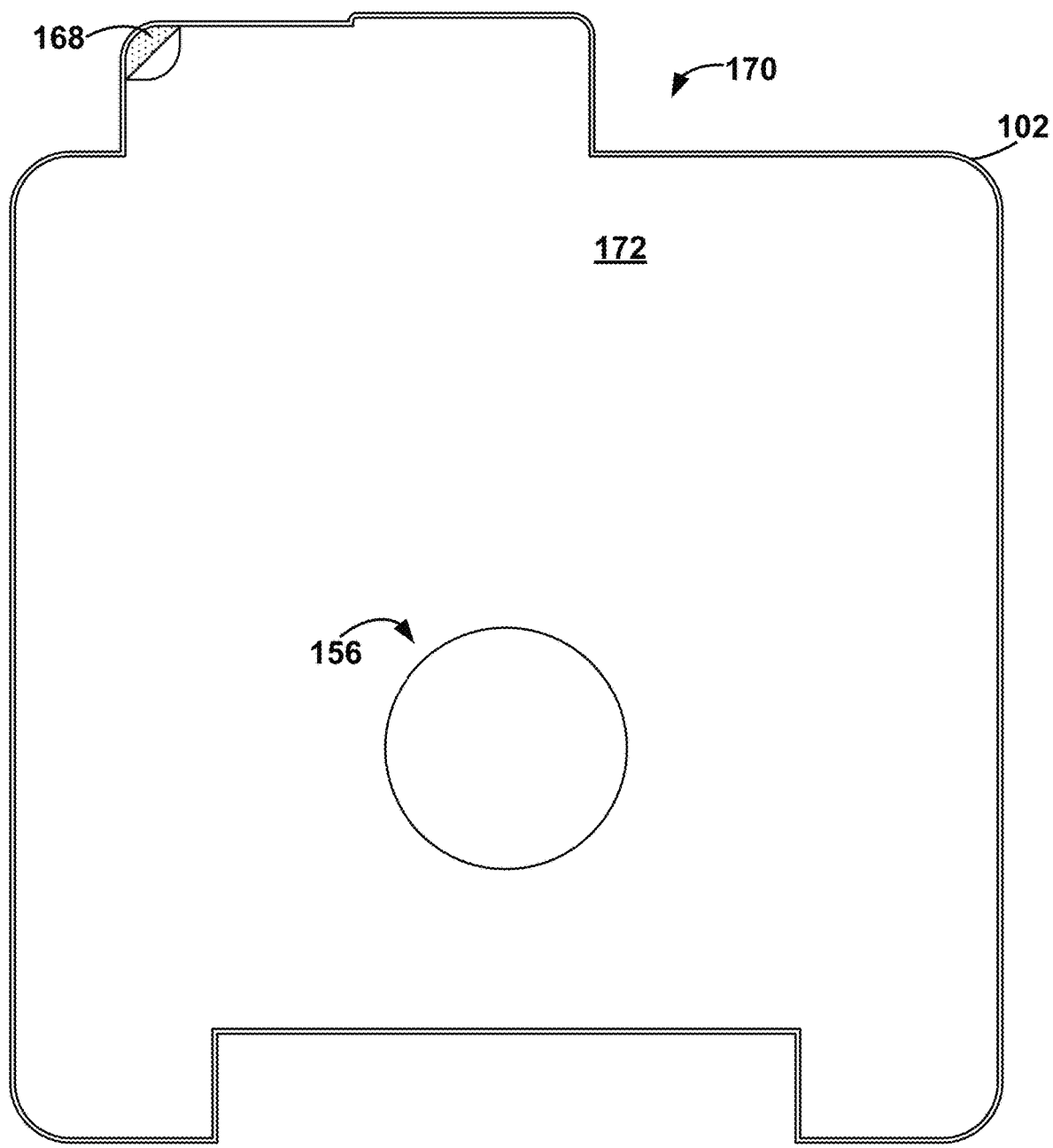
FIG. 24 is a rear view of a wire clamping device, according to an embodiment of the disclosure.

FIG. 24 is a rear view of the wire clamping device 100. As shown, an adhesive material 168 (e.g., a double-sided foam adhesive strip, a glue, etc.) is positioned on an opposing exterior surface 170 of the base 102. The adhesive material 168 may be covered with a backing sheet 172 (e.g., paper), to be removed when it is time to attach the device 100 to a subject's skin, for example.

Figure 24A:
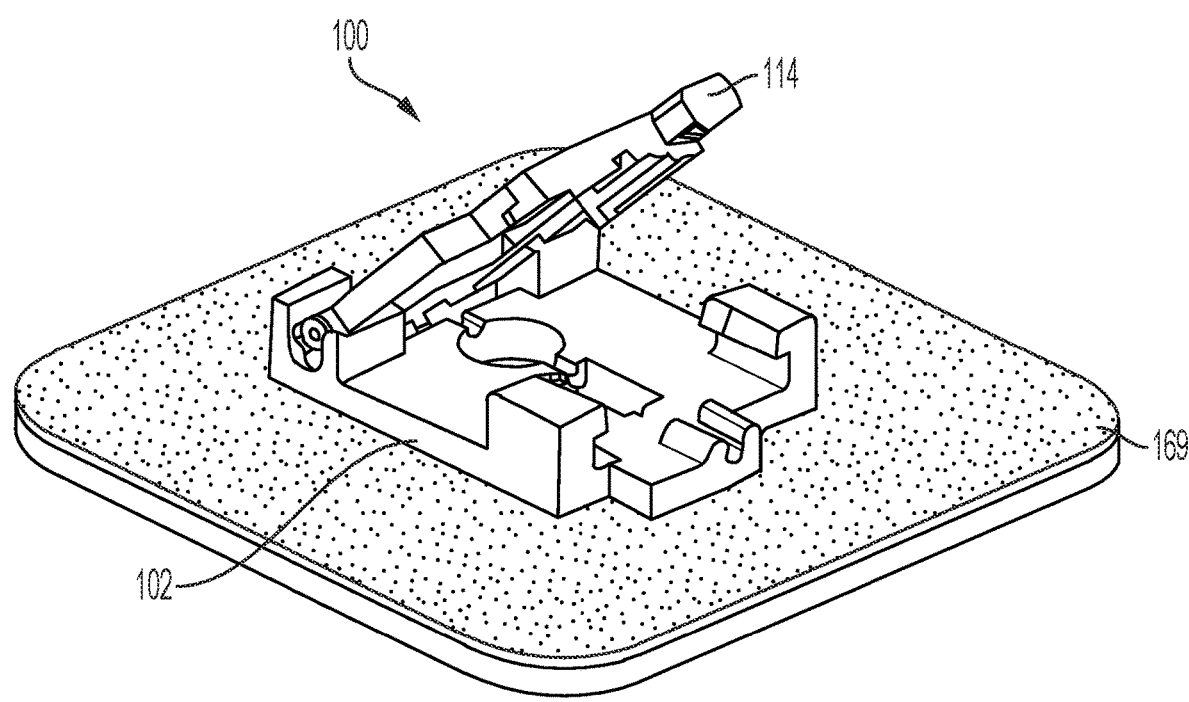
FIG. 24A is a perspective view of a wire clamping device affixed to an application pad, according to an embodiment of the disclosure.

FIG. 24A shows the base 102 affixed to an application pad 169. The application pad 169 can take the form of a thin sheet of cotton gauze, but other examples are possible. The base 102 can be affixed to the application pad 169 via any suitable adhesive material.

Figure 24B:
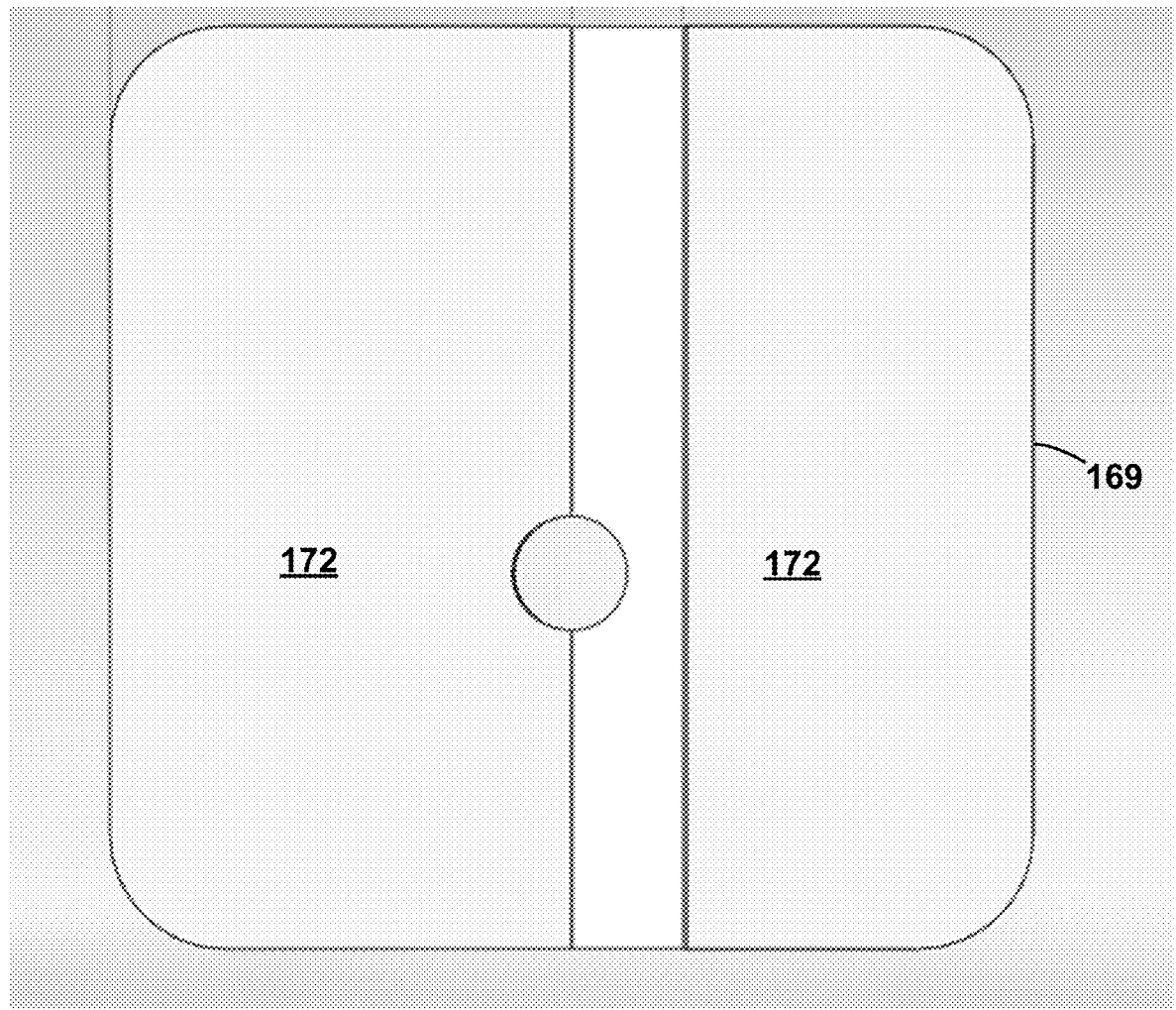
FIG. 24B is a rear view of an application pad, according to an embodiment of the disclosure.

FIG. 24B is a rear view of the application pad 169. The sheet 172 discussed above can also be affixed to the application pad 169 via adhesive material (e.g., facing away from the device 100), to be removed when it is time to attach the device 100 to a subject's skin, for example. As shown in FIG. 24B, the sheet 172 could be split into two pieces for easier removal.

Figure 25:
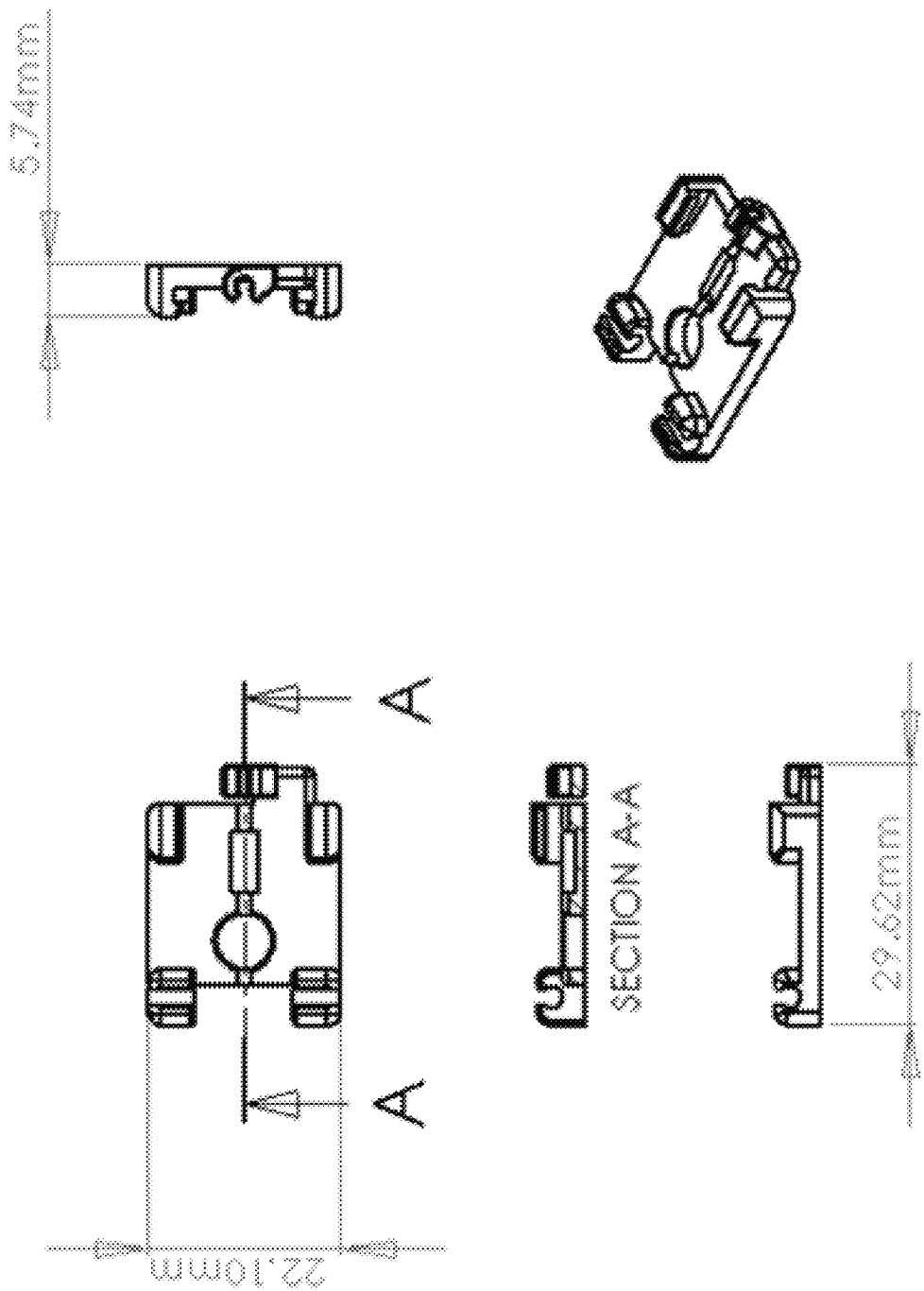
FIG. 25 includes multiple views of a base of a wire clamping device, according to an embodiment of the disclosure.

FIG. 25 includes multiple views of the base 102 of the wire clamping device 100. The dimensions shown are provided as examples only and are not meant to be limiting.

Figure 26:
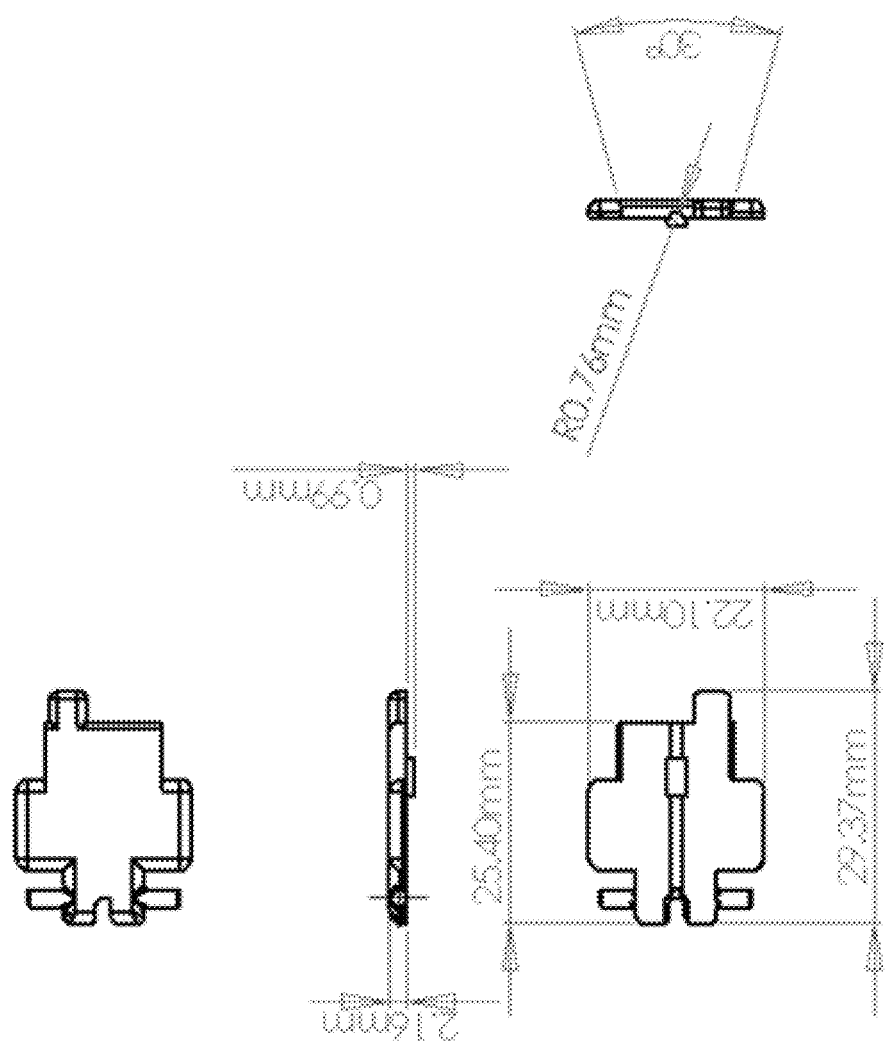
FIG. 26 includes multiple views of an arm of a wire clamping device, according to an embodiment of the disclosure.

FIG. 26 includes multiple views of the arm 114 of the wire clamping device 100. The dimensions shown are provided as examples only and are not meant to be limiting.

Figure 27:
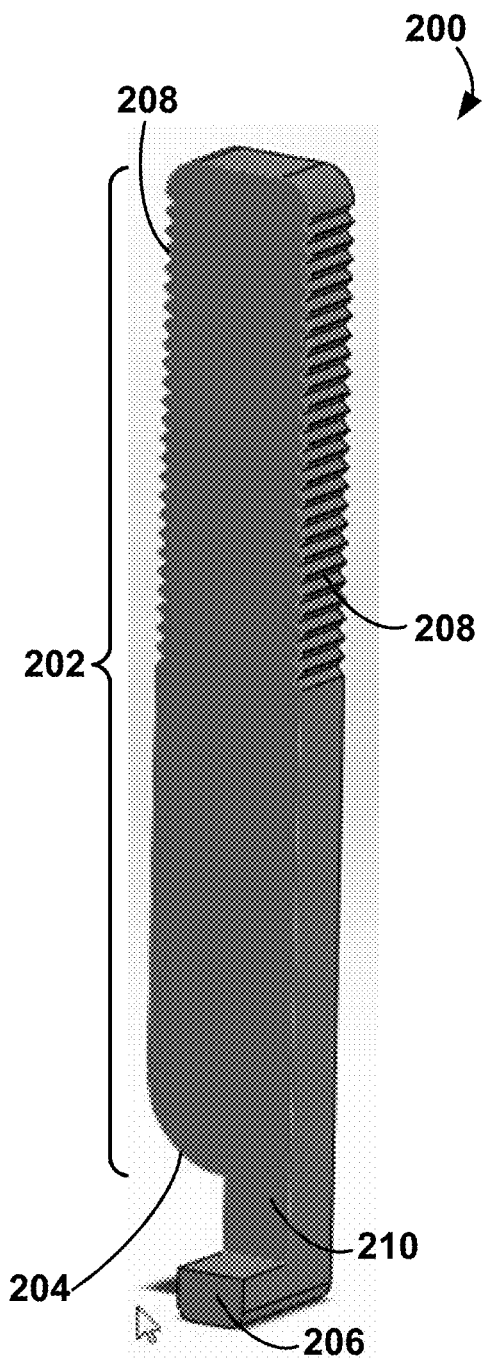
FIG. 27 is a perspective view of a tool for opening a wire clamping device, according to an embodiment of the disclosure.

FIG. 27 is a perspective view of a tool 200 for opening a wire clamping device, such as the wire clamping device 100. The tool 200 includes a handle 202 having a rounded surface 204 and a protrusion 206 that is substantially perpendicular to the handle (e.g., within 15 degrees, 10 degrees, 5, degrees, or 2.5 degrees of being perpendicular). The rounded surface 204 is configured to be on top of the attachment component 110 when the protrusion 206 is underneath the extension 164 of the arm 114. The handle 202 further includes a textured surface 208. Additionally, the tool 200 includes a connecting section 210 that connects the handle 202 to the protrusion 206 of the tool 200. The connecting section 210 is configured to be positioned against the surface 173 when the rounded surface 204 is on top of the surface 171 (see FIGS. 7 and 34 for more detail).

Figure 28:
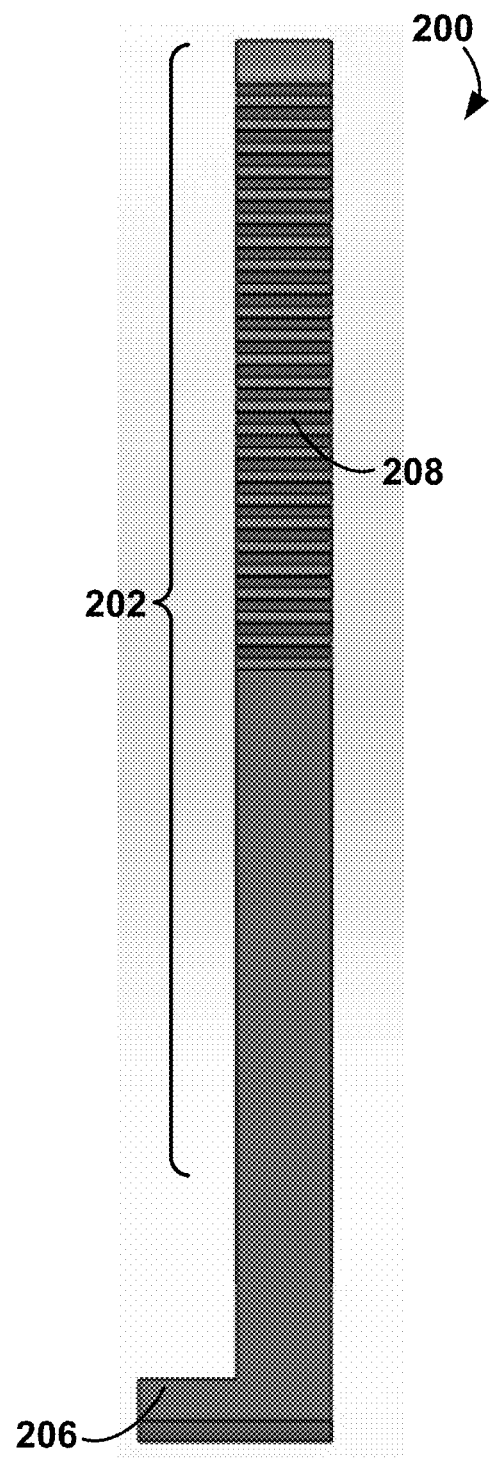
FIG. 28 is a front view of a tool for opening a wire clamping device, according to an embodiment of the disclosure.

FIG. 28 is a front view of the tool 200.

Figure 29:
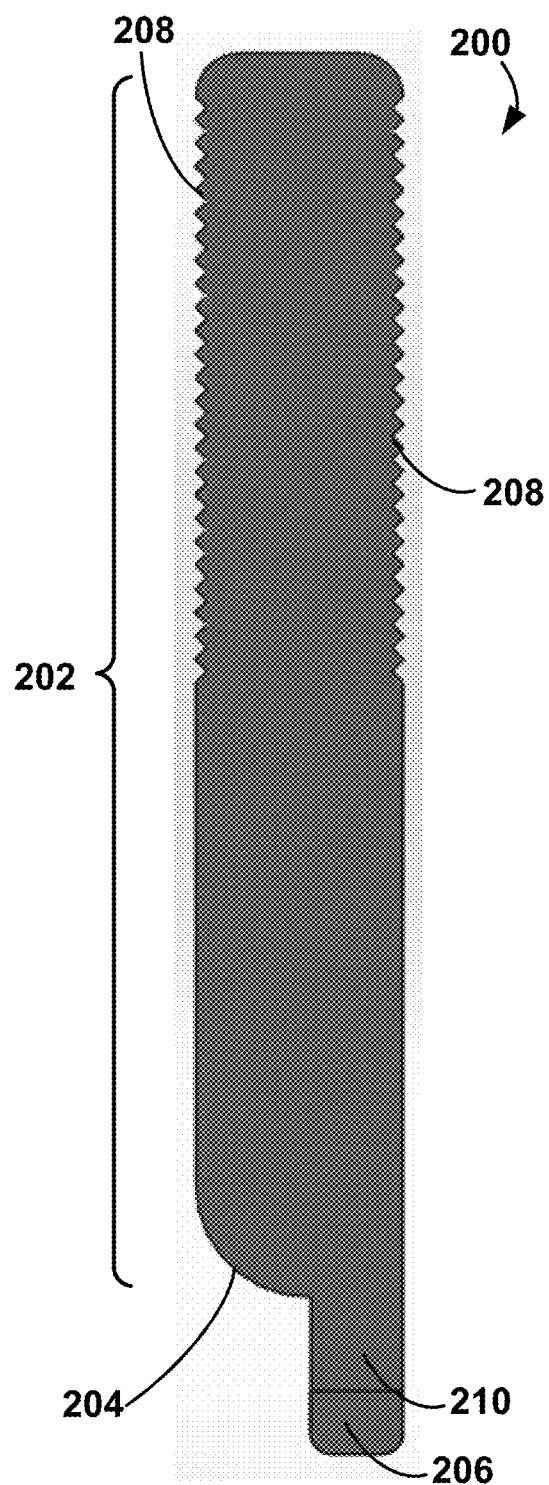
FIG. 29 is a side view of a tool for opening a wire clamping device, according to an embodiment of the disclosure.

FIG. 29 is a side view of the tool 200.

Figure 30:
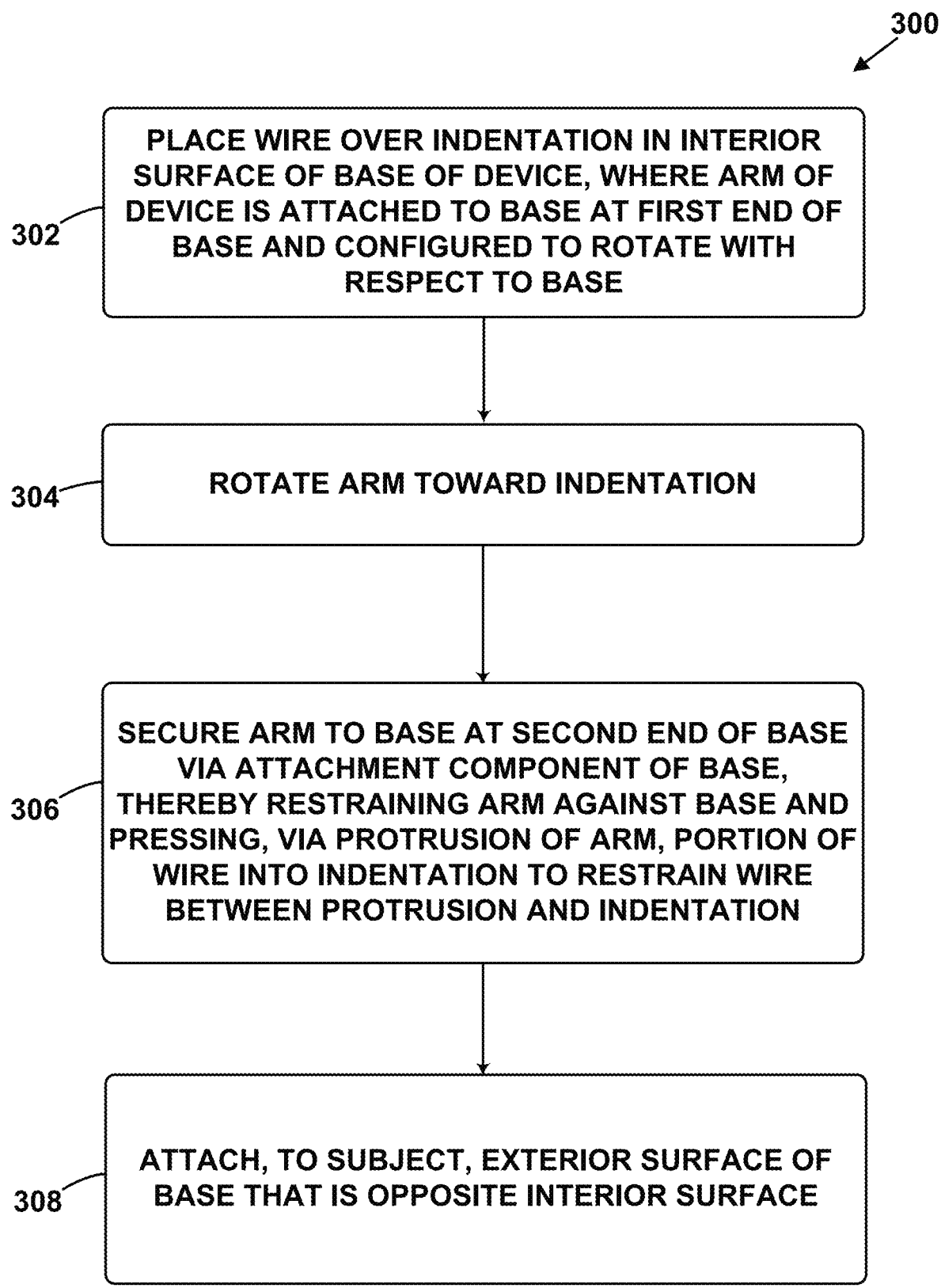
FIG. 30 is a block diagram of a method for using a wire clamping device, according to an embodiment of the disclosure.

FIG. 30 is a block diagram of a method 300 for using a wire clamping device, such as the wire clamping device 100.

At block 302, the method 300 includes placing a wire over an indentation in an interior surface of a base of the device. In this context, an arm of the device is attached to the base at a first end of the base and configured to rotate with respect to the base. Referring to FIG. 1, for example, the wire 148 may be placed over the indentation 104 in the interior surface 134 of the base 102. In various embodiments, a diameter of the wire is within a range of 0.5 millimeters (mm) to 1.5 mm, 0.75 mm to 1.25 mm, or 0.95 mm to 1.05 mm.

At block 304, the method 300 includes rotating the arm toward the indentation. At block 306, the method 300 includes securing the arm to the base at a second end of the base via an attachment component of the base, thereby restraining the arm against the base and pressing, via a protrusion of the arm, a portion of the wire into the indentation to restrain the wire between the protrusion and the indentation.

For example, the arm 114 may be rotated toward the indentation 104. The arm 114 may be secured to the base 102 at the end 112 of the base 102 via the attachment component 110, thereby restraining the arm 114 against the base 102 and pressing, via the protrusion 116, the portion 146 of the wire 148 into the indentation 104 to restrain the wire 148 between the protrusion 116 and the indentation 104 (see FIG. 7).

At block 308, the method 300 includes attaching, to a subject, an exterior surface of the base that is opposite the interior surface. Referring to FIG. 32, for example, the exterior surface 170 (shown in FIG. 24) that is opposite the interior surface 134 may be attached (e.g., adhesively) to a back 502 of a subject 500. In some embodiments, this may involve attaching the exterior surface 170 to the subject 500 such that the hole 156 in the base 102 is over a point 508 (e.g., a puncture wound) at which the wire 148 is inserted percutaneously into the subject 500 (see FIG. 31).

Figure 31:
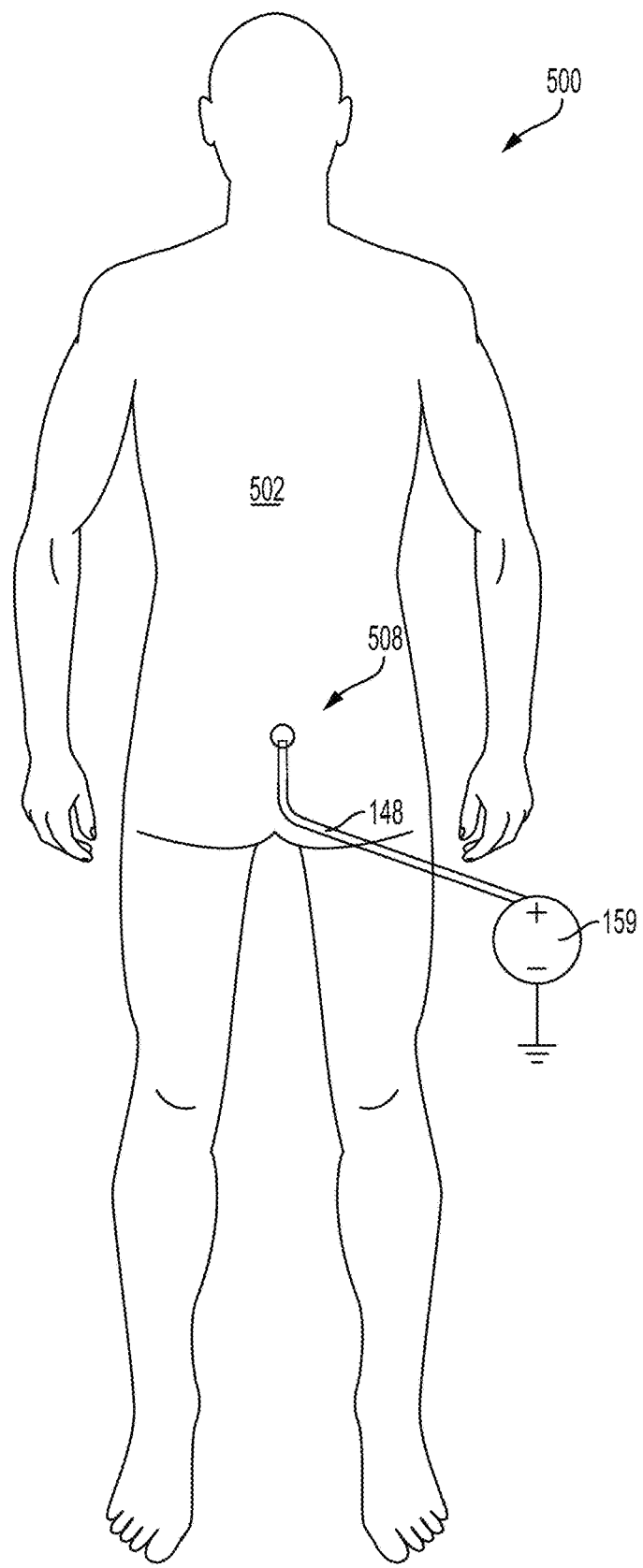
FIG. 31 is a rear view of a subject with a percutaneously inserted wire, according to an embodiment of the disclosure.
Figure 32:
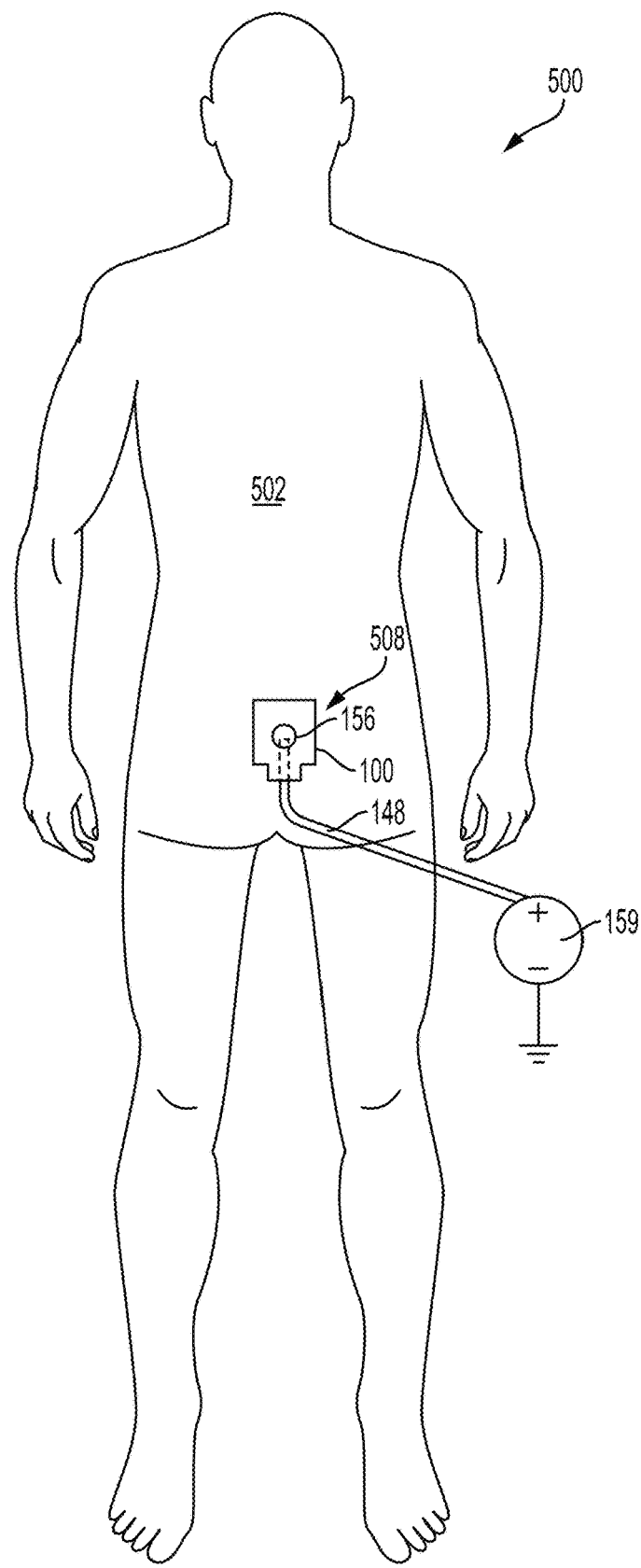
FIG. 32 is a rear view of a subject with a wire clamping device attached to skin, according to an embodiment of the disclosure.
Figure 32A:
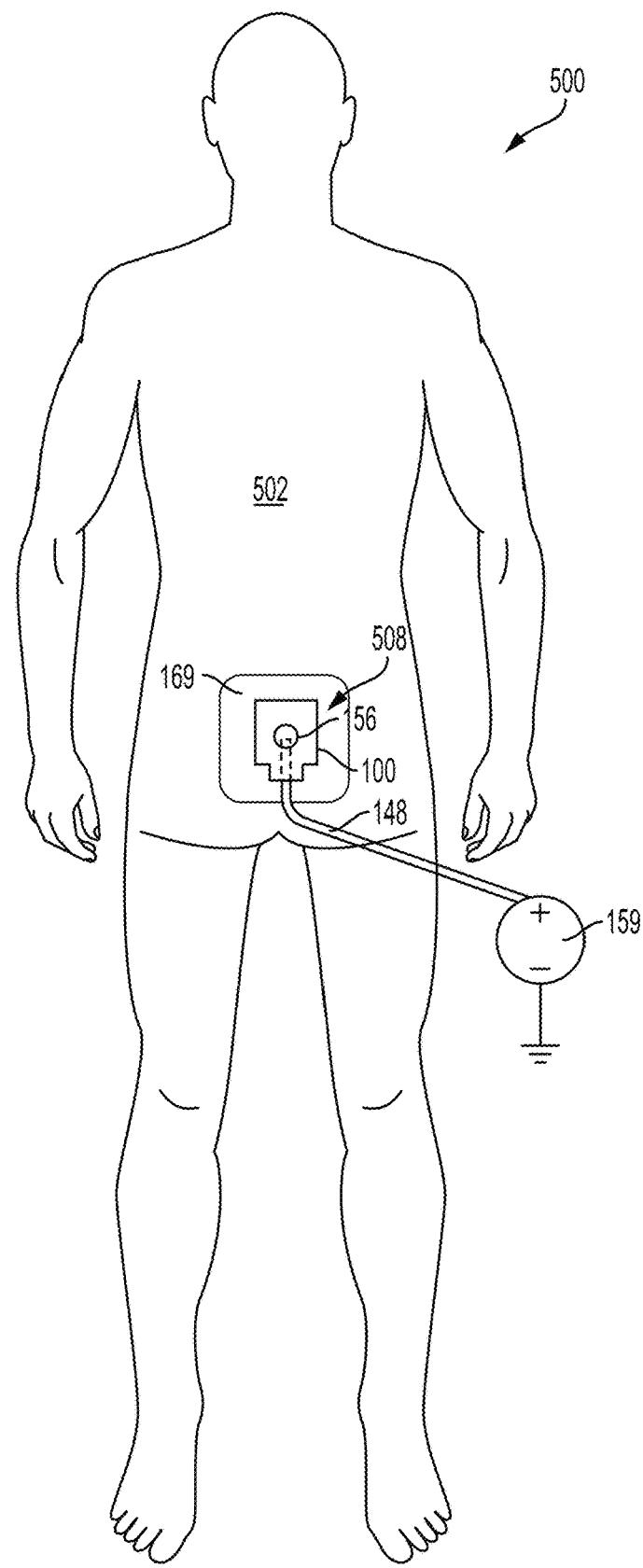
FIG. 32A is a rear view of a subject with a wire clamping device attached to skin, according to an embodiment of the disclosure.

Referring to FIG. 32A as another example, the application pad 169 that is opposite the interior surface 134 may be attached (e.g., adhesively) to the back 502 of the subject 500. In some embodiments, this may involve attaching the application pad 169 to the subject 500 such that the hole 156 in the base 102 is over a point 508 (e.g., a puncture wound) at which the wire 148 is inserted percutaneously into the subject 500 (see FIG. 31).

FIG. 31 is a rear view of the subject 500. In some embodiments, the method 300 may involve inserting a portion (e.g., an end) of the wire 148 percutaneously into the subject 500 (e.g., at point 508). A puncture wound can be formed in the back 502 of the subject 500 (e.g., via a needle) and the wire 148 may be inserted through the puncture wound. Next, the wire 148 can be routed through (i) the hole 156 or (ii) the notch 160 and the groove 158. When routed through the groove 158, the groove 158 helps secure the wire 148 when the device 100 is closed. Additionally, the wire 148 may be routed through the wire guide 150 and connected to a power supply 159 (see FIG. 32).

In some embodiments, pressing the portion 146 of the wire 148 into the indentation 104 causes the wire 148 to bend, as shown in FIG. 1. Additionally, pressing the portion 146 of the wire 148 into the indentation 104 causes the portion 146 of the wire to be 0.1 millimeters (mm) to 1.0 mm, 0.25 mm to 0.75 mm, or 0.45 mm to 0.55 mm offset from other portions of the wire 148 that are enclosed within the device 100. In particular embodiments, securing the arm 114 to the base 102 may include securing the arm 114 to the base 102 such that the wire 148 is positioned within the portions 162A and/or 162B of the groove of the arm 114.

Additionally, some embodiments may involve causing an electrical current to pass through the wire 148 into the subject 500. For example, the power supply 159 may provide current that flows through the wire 148 into the subject 500. These methods may be used to treat one or more of Post Laminectomy Syndrome, Lumbar Radiculopathy, Cervical Radiculopathy, Complex Regional Pain Syndrome, Idiopathic peripheral neuropathy, causalgia, or chronic pain syndrome.

Figure 33:
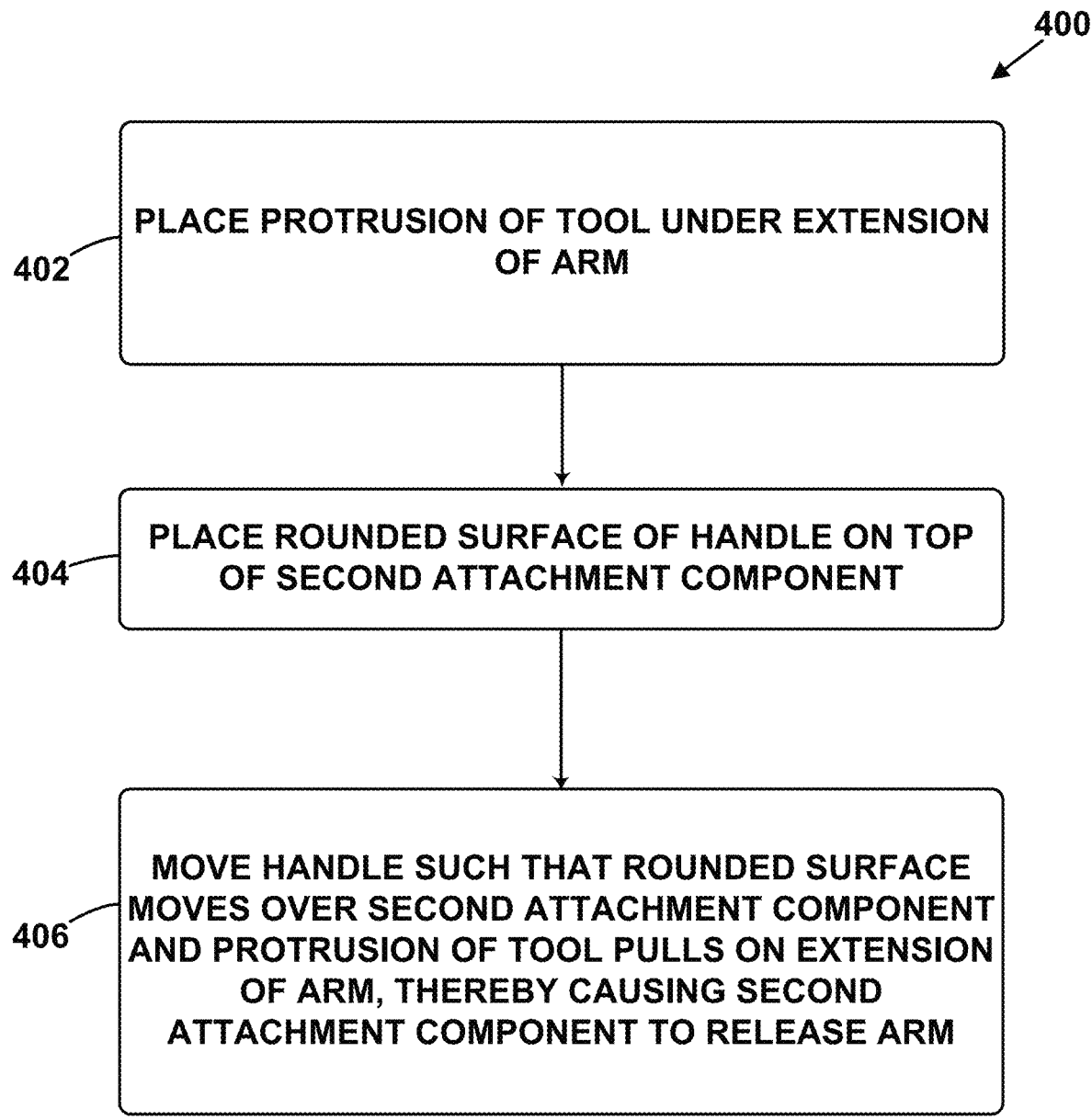
FIG. 33 is a block diagram of a method for using an opening tool to open a wire clamping device, according to an embodiment of the disclosure.

FIG. 33 is a block diagram of a method 400 for using an opening tool, such as the opening tool 200, to open a wire clamping device, such as the wire clamping device 100.

Figure 34:
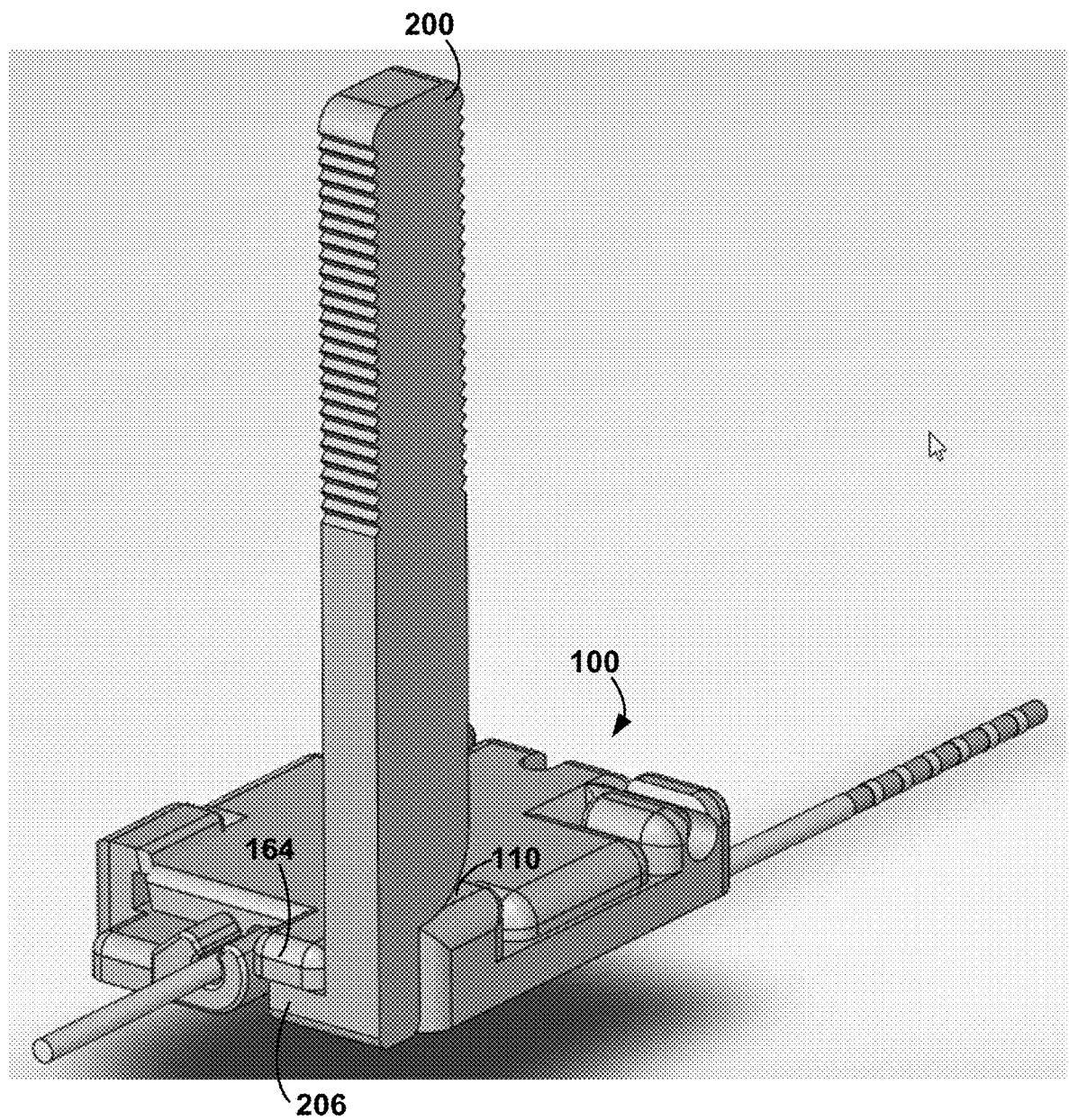
FIG. 34 depicts the use of an opening tool to open a wire clamping device, according to an embodiment of the disclosure.

At block 402, the method 400 includes placing the protrusion of the tool under the extension of the arm. Referring to FIG. 34, for example, the protrusion 206 may be placed under the extension 164.

At block 404, the method 400 includes placing the rounded surface of the handle on top of the second attachment component. For example, the rounded surface 204 may be placed on top of the attachment component 110.

Figure 35:
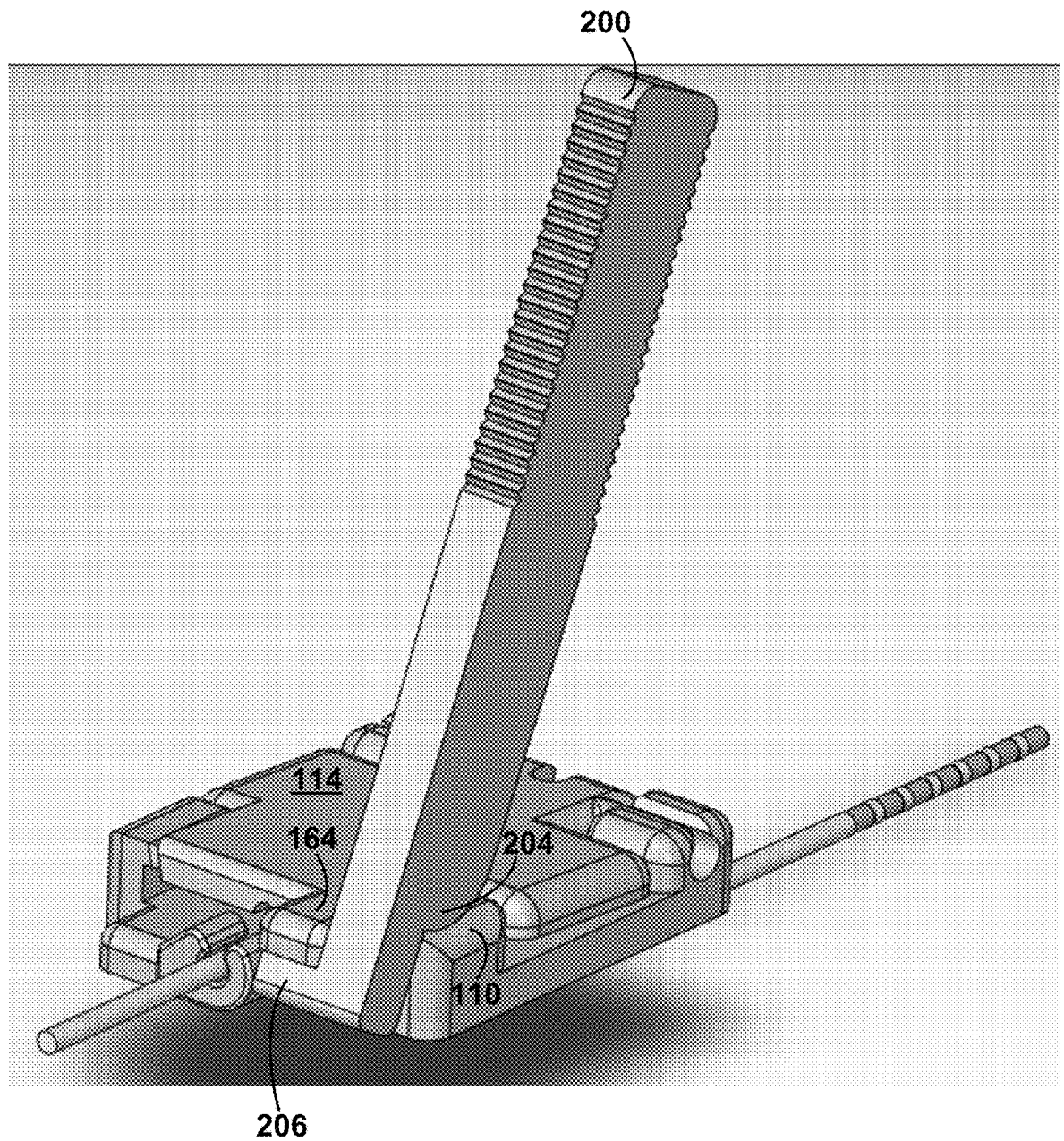
FIG. 35 depicts the use of an opening tool to open a wire clamping device, according to an embodiment of the disclosure.

At block 406, the method 400 includes moving the handle such that the rounded surface moves over the second attachment component and the protrusion of the tool pulls on the extension of the arm, thereby causing the second attachment component to release the arm. As shown in FIG. 35, for example, the handle 202 may be moved such that the rounded surface 204 moves over the attachment component 110 and the protrusion 206 pulls on the extension 164, thereby causing the attachment component 110 to release the arm 114. That is, the protrusion 206 may pull the extension 164 with enough force that the arm 114 "pops" out from underneath the attachment component 110.

Embodiments of the present disclosure can thus relate to one of the enumerated example embodiments (EEEs) listed below.

EEE 1 is a wire clamping device that includes a base that includes an indentation, a first attachment component at a first end of the base, and a second attachment component at a second end of the base that is opposite the first end. The wire clamping device further includes an arm that includes a protrusion and a third attachment component that is attached to the first attachment component. The arm is configured to rotate with respect to the first attachment component to a position at which the arm is restrained by the second attachment component against the base and at least a portion of the protrusion is within the indentation or aligned with the indentation.

EEE 2 is the device of EEE 1, wherein a depth of the indentation is within a range of 1.0 millimeters (mm) to 2.0 mm, 1.25 mm to 1.75 mm, or 1.45 mm to 1.55 mm.

EEE 3 is the device of any of EEEs 1-2, wherein a length of the indentation along an axis that is perpendicular to an axis of rotation of the arm is within a range of 4.5 millimeters (mm) to 5.5 mm, 4.75 mm to 5.25 mm, or 4.95 mm to 5.05 mm.

EEE 4 is the device of any of EEEs 1-3, wherein a width of the indentation along an axis that is parallel to an axis of rotation of the arm is within a range of 1.5 millimeters (mm) to 2.5 mm, 1.75 mm to 2.25 mm, or 1.95 mm to 2.05 mm.

EEE 5 is the device of any of EEEs 1-4, wherein the third attachment component is configured to snap into the first attachment component to form a hinged connection.

EEE 6 is the device of any of EEEs 1-5, wherein the indentation is on an interior surface of the base, wherein the second attachment component comprises one or more surfaces that are sloped with respect to the interior surface, and wherein the arm comprises one or more surfaces that are sloped with respect to the interior surface and are configured to move against the respective one or more sloped surfaces of the second attachment component as the arm is rotated toward the base.

EEE 7 is the device of any of EEEs 1-6, wherein the second attachment component includes one or more extensions configured to protrude over the arm to restrain the arm against the base.

EEE 8 is the device of any of EEEs 1-7, wherein the protrusion has a rectangular face.

EEE 9 is the device of any of EEEs 1-8, wherein the protrusion extends below an interior surface of the arm at a depth within a range of 0.5 mm to 1.5 mm, 0.75 mm to 1.25 mm, or 0.95 mm to 1.05 mm.

EEE 10 is the device of any of EEEs 1-9, wherein the protrusion is configured to press a portion of a wire into the indentation.

EEE 11 is the device of any of EEEs 1-10, wherein the base further comprises a wire guide at the second end of the base, wherein the wire guide is configured to receive a wire.

EEE 12 is the device of EEE 11, wherein the wire guide is configured to resist motion the wire in a direction that is parallel with an axis of rotation of the arm.

EEE 13 is the device of any of EEEs 11-12, wherein the wire guide is configured to resist motion of the wire in a direction that is perpendicular with an axis of rotation of the arm.

EEE 14 is the device of any of EEEs 11-13, wherein the wire guide is configured to clasp the wire.

EEE 15 is the device of any of EEEs 11-14, wherein the wire guide has an inner diameter within a range of 0.5 millimeters (mm) to 1.5 mm, 0.75 mm to 1.25 mm, or 0.95 mm to 1.05 mm.

EEE 16 is the device of any of EEEs 1-15, wherein the base further comprises a hole between the indentation and the first end of the base.

EEE 17 is the device of any of EEEs 1-16, wherein the base further comprises a groove that is configured to receive a wire.

EEE 18 is the device of EEE 17, wherein the groove of the base is at the first end of the base.

EEE 19 is the device of any of EEEs 1-18, wherein the arm further comprises a notch adjacent to the groove of the base.

EEE 20 is the device of EEE 19, wherein the notch is configured to receive a wire.

EEE 21 is the device of any of EEEs 1-20, wherein the arm further comprises a groove that is configured to receive a wire.

EEE 22 is the device of EEE 21, wherein the groove of the arm comprises: a first portion on a first side of the protrusion; and a second portion on an opposing second side of the protrusion.

EEE 23 is the device of EEE 22, wherein the protrusion is configured to press a portion of a wire into the indentation, and wherein the first portion of the groove and the second portion of the groove are configured to resist motion of the wire in a direction that is parallel to an axis of rotation of the arm.

EEE 24 is the device of any of EEEs 21-23, wherein the protrusion is wider than the groove of the arm in a direction that is parallel to an axis of rotation of the arm.

EEE 25 is the device of any of EEEs 1-24, wherein the arm comprises an extension that is configured to protrude past a portion of the base adjacent to the second end of the base when the arm is restrained by the second attachment component.

EEE 26 is the device of any of EEEs 1-25, wherein the indentation is positioned on an interior surface of the base, the device further comprising: an adhesive material positioned on an opposing exterior surface of the base.

EEE 27 is the device of EEE 26, further comprising a backing sheet that covers the adhesive material.

EEE 28 is the device of any of EEEs 1-27, wherein the arm is configured to move underneath the second attachment component to be restrained by the second attachment component against the base.

EEE 29 is the device of any of EEEs 1-28, wherein the arm is configured to rotate with respect to the first attachment component to a position at which no portion of the protrusion extends beyond any boundary of the indentation in a direction parallel to the interior surface of the base.

EEE 30 is a tool for opening the device of any of EEEs 1-29, the tool comprising: a handle comprising a rounded surface; and a protrusion that is substantially perpendicular to the handle, wherein the rounded surface of the handle is configured to be on top of the second attachment component when the protrusion of the tool is underneath the extension of the arm.

EEE 31 is the tool of EEE 30, wherein the handle has a textured surface.

EEE 32 is the tool of any of EEEs 30-31, wherein the second attachment component comprises a first surface and a second surface that is perpendicular to the first surface, the tool further comprising: a connecting section that connects the handle to the protrusion of the tool, wherein the connecting section is configured to be positioned against the first surface when the rounded surface of the handle is on top of the second surface.

EEE 33 is a method for using the wire clamping device of any of EEEs 1-29, the method comprising: placing a wire over an indentation in an interior surface of a base of the device, wherein an arm of the device is attached to the base at a first end of the base and configured to rotate with respect to the base; rotating the arm toward the indentation; securing the arm to the base at a second end of the base via an attachment component of the base, thereby restraining the arm against the base and pressing, via a protrusion of the arm, a portion of the wire into the indentation to restrain the wire between the protrusion and the indentation; and attaching, to a subject, an exterior surface of the base that is opposite the interior surface.

EEE 34 is the method of EEE 33, wherein a diameter of the wire is within a range of 0.5 mm to 1.5 mm, 0.75 mm to 1.25 mm, or 0.95 mm to 1.05 mm.

EEE 35 is the method of any of EEEs 33-34, further comprising inserting a portion of the wire percutaneously into the subject.

EEE 36 is the method of any of EEEs 33-35, further comprising inserting the wire through a hole in the base between the indentation and the first end of the base.

EEE 37 is the method of any of EEEs 35-36, wherein attaching the exterior surface of the base to the subject comprises attaching the exterior surface of the base to the subject such that the hole in the base is over a point at which the wire is inserted percutaneously into the subject.

EEE 38 is the method of any of EEEs 33-35, further comprising inserting the wire through a notch in the arm.

EEE 39 is the method of EEE 38, further comprising placing the wire into a groove in the interior surface of the base that is adjacent to the notch in the arm, wherein securing the arm to the base causes the wire to be restrained within the groove in the interior surface.

EEE 40 is the method of any of EEEs 33-39, further comprising placing the wire into a wire guide at the second end of the base.

EEE 41 is the method of any of EEEs 33-40, wherein pressing the portion of the wire into the indentation causes the wire to bend.

EEE 42 is the method of any of EEEs 33-41, wherein pressing the portion of the wire into the indentation causes the portion of the wire to be 0.1 millimeters (mm) to 1.0 mm, 0.25 mm to 0.75 mm, or 0.45 mm to 0.55 mm offset from other portions of the wire that are enclosed within the device.

EEE 43 is the method of any of EEEs 33-42, wherein the arm further comprises a groove, and wherein securing the arm to the base comprises securing the arm to the base such that the wire is positioned within the groove of the arm.

EEE 44 is the method of any of EEEs 35-43, further comprising causing an electrical current to pass through the wire into the subject, wherein the method is performed to treat one or more of Post Laminectomy Syndrome, Lumbar Radiculopathy, Cervical Radiculopathy, Complex Regional Pain Syndrome, Idiopathic peripheral neuropathy, causalgia, or chronic pain syndrome.

EEE 45 is a method for using the opening tool of any of EEEs 30-32 to open the clamping device of any of EEEs 1-29, the method comprising: placing the protrusion of the tool under the extension of the arm; placing the rounded surface of the handle on top of the second attachment component; and moving the handle such that the rounded surface moves over the second attachment component and the protrusion of the tool pulls on the extension of the arm, thereby causing the second attachment component to release the arm.

While various example aspects and example embodiments have been disclosed herein, other aspects and embodiments will be apparent to those skilled in the art. The various example aspects and example embodiments disclosed herein are for purposes of illustration and are not intended to be limiting, with the true scope and spirit being indicated by the following claims.

What is claimed is:

1. A wire clamping device comprising:
a base comprising:
an indentation within an interior surface of the base;
a first attachment component at a first end of the base; and
a second attachment component at a second end of the base that is opposite the first end; and
an arm comprising:
a protrusion extending from an interior surface of the arm; and
a third attachment component that is attached to the first attachment component,
wherein the arm is configured to rotate with respect to the first attachment component to a position at which the arm is restrained by the second attachment component against the base and at least a portion of the protrusion is within the indentation or aligned with the indentation,
wherein the protrusion is configured to press a portion of a wire into the indentation with a force that is transverse to the interior surface of the base and transverse to the interior surface of the arm, and
wherein the arm further comprises a groove that is configured to receive the wire while the force is applied to the wire.

2. The wire clamping device of claim 1, wherein the third attachment component is configured to snap into the first attachment component to form a hinged connection.

3. The wire clamping device of claim 1,
wherein the second attachment component comprises one or more surfaces that are sloped with respect to the interior surface of the base, and
wherein the arm comprises one or more surfaces that are sloped with respect to the interior surface of the base and are configured to move in direct contact with the one or more sloped surfaces of the second attachment component as the arm is rotated toward the base.

4. The wire clamping device of claim 1, wherein the second attachment component includes one or more extensions configured to protrude over the arm in a direction parallel to the interior surface of the base to restrain the arm against the base.

5. The wire clamping device of claim 1, further comprising: an adhesive material positioned on an exterior surface of the base that opposes the interior surface of the base.

6. The wire clamping device of claim 1, further comprising an application pad comprising gauze, the application pad being affixed to an exterior surface of the base, the application pad having an adhesive material disposed thereon that faces away from the exterior surface of the base.

7. The wire clamping device of claim 1, wherein the base further comprises a wire guide at the second end of the base, wherein the wire guide is configured to receive the wire.

8. The wire clamping device of claim 7, wherein the wire guide is configured to resist motion of the wire in a direction that is parallel with an axis of rotation of the arm.

9. The wire clamping device of claim 7, wherein the wire guide is configured to resist motion of the wire in a direction that is perpendicular with an axis of rotation of the arm.

10. The wire clamping device of claim 1, wherein the arm further comprises a notch adjacent to a groove of the base.

11. The wire clamping device of claim 10, wherein the notch is configured to receive the wire.

12. The wire clamping device of claim 1, wherein the groove of the arm comprises:
a first portion on a first side of the protrusion; and
a second portion on an opposing second side of the protrusion.

13. The wire clamping device of claim 12,
wherein the protrusion is configured to press the portion of the wire into the indentation, and
wherein the first portion of the groove and the second portion of the groove are configured to resist motion of the wire in a direction that is parallel to an axis of rotation of the arm.

14. The wire clamping device of claim 1, wherein the protrusion is wider than the groove of the arm in a direction that is parallel to an axis of rotation of the arm.

15. The wire clamping device of claim 1, wherein the arm comprises an extension that is configured to protrude past a portion of the base adjacent to the second end of the base in a direction that is parallel to the interior surface of the base when the arm is restrained by the second attachment component.

16. The wire clamping device of claim 1, wherein the arm is configured to move underneath the second attachment component to be restrained by the second attachment component against the base.

17. The wire clamping device of claim 1, wherein the arm is configured to rotate with respect to the first attachment component to a position at which no portion of the protrusion extends beyond any boundary of the indentation in a direction parallel to the interior surface of the base.

18. A method for using a wire clamping device, the method comprising:
placing a wire over an indentation within an interior surface of a base of a wire clamping device, wherein an arm of the wire clamping device is attached to the base at a first end of the base and configured to rotate with respect to the base;
rotating the arm toward the indentation;
securing the arm to the base at a second end of the base via an attachment component of the base, thereby restraining the arm against the base and pressing, via a protrusion of the arm that extends from an interior surface of the arm and via a force that is transverse to the interior surface of the base and transverse to the interior surface of the arm, a portion of the wire into the indentation to restrain the wire between the protrusion and the indentation;
receiving, via a groove of the arm, the wire while the force is applied to the wire; and
attaching, to a subject, an exterior surface of the base that is opposite the interior surface of the base.

19. The method of claim 18, wherein rotating the arm toward the indentation comprises moving one or more sloped surfaces of the arm in direct contact with respective one or more sloped surfaces of a second attachment component of the base that are sloped with respect to the interior surface of the base.

20. The method of claim 18, wherein the base includes one or more extensions, and wherein securing the arm to the base comprises causing the one or more extensions to protrude over the arm in a direction parallel to the interior surface of the base to restrain the arm against the base.

21. The wire clamping device of claim 1, further comprising a hole in the interior surface of the base, wherein the hole is adjacent to the indentation and configured to receive the wire while the force is applied to the wire.

* * * * *